(12) United States Patent
Yun et al.

(10) Patent No.: US 9,517,990 B2
(45) Date of Patent: *Dec. 13, 2016

(54) NEGATIVE DIELECTRIC ANISOTROPIC LIQUID CRYSTAL COMPOUNDS CONTAINING 2,3-DIFLUOROPHENYL GROUP, AND PREPARATION METHOD AND USE THEREOF

(71) Applicant: Shijiazhuang Chengzhi Yonghua Display Materials Co., Ltd., Hebei Province (CN)

(72) Inventors: Guoliang Yun, Hebei Province (CN); Ruimao Hua, Hebei Province (CN); Kui Wang, Hebei Province (CN); Zefeng Hou, Hebei Province (CN); Lei Zhao, Hebei Province (CN); Gang Wen, Hebei Province (CN); Lianbo Mao, Hebei Province (CN)

(73) Assignee: Shijiazhuang Chenzhi Yonghua Display Materials Co., Ltd., Shi Jia Zhuang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/407,652

(22) PCT Filed: Nov. 19, 2013

(86) PCT No.: PCT/CN2013/001416
§ 371 (c)(1),
(2) Date: Dec. 12, 2014

(87) PCT Pub. No.: WO2014/079147
PCT Pub. Date: May 30, 2014

(65) Prior Publication Data
US 2015/0152330 A1    Jun. 4, 2015

(30) Foreign Application Priority Data
Nov. 23, 2012    (CN) .......................... 2012 1 0483290

(51) Int. Cl.
C07C 27/00    (2006.01)
C07C 43/247    (2006.01)
(Continued)

(52) U.S. Cl.
CPC .......... *C07C 43/247* (2013.01); *C07C 43/225* (2013.01); *C09K 19/30* (2013.01); *C09K 19/3066* (2013.01);
(Continued)

(58) Field of Classification Search
CPC ...................................................... C07C 27/00
(Continued)

(56) References Cited

U.S. PATENT DOCUMENTS

2008/0206490 A1* 8/2008 Reiffenrath et al. .......... 428/1.1
2011/0309300 A1    12/2011 Masukawa et al.

FOREIGN PATENT DOCUMENTS

| CN | 103030534 | 4/2013 |
| CN | 103074073 | 5/2013 |
| CN | 103254907 | 8/2013 |

OTHER PUBLICATIONS

International Search Report dated Jan. 13, 2014; International Application No. PCT/CN2013/001416; International Filing Date: Nov. 19, 2013; 5 pages.
(Continued)

Primary Examiner — Chanceity Robinson
(74) Attorney, Agent, or Firm — Blank Rome LLP

(57) ABSTRACT

A negative dielectric anisotropic liquid crystal compound containing 2,3-difluorophenyl, and a preparation method and use thereof are disclosed. The compound has a general structural formula as shown in Formula I. The negative dielectric anisotropic liquid crystal compound has a negative dielectric anisotropy (Δ∈), and has cyclobutyl or cyclopentyl as a terminal group. Compared with conventional liquid crystal compounds with a flexible alkyl chain as a terminal group, the compound of Formula I according to the present
(Continued)

invention has the advantage of high clearing point, and enables extension of the application range of a liquid crystal mixture because a positive correlation exists between the clearing points of the liquid crystal mixture and monomer liquid crystal compounds. In addition, the compound can increase the absolute value of the negative dielectric constant of the liquid crystal mixture, thus having an important application value.

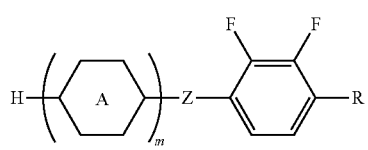

Formula I

15 Claims, 3 Drawing Sheets

(51) Int. Cl.
C07C 43/225 (2006.01)
C09K 19/30 (2006.01)
C09K 19/12 (2006.01)

(52) U.S. Cl.
CPC ..... *C09K 19/3068* (2013.01); *C09K 2019/122* (2013.01); *C09K 2019/123* (2013.01); *C09K 2019/3004* (2013.01); *C09K 2019/3009* (2013.01); *C09K 2019/3016* (2013.01); *C09K 2019/3027* (2013.01); *C09K 2019/3036* (2013.01); *C09K 2019/3075* (2013.01); *C09K 2019/3096* (2013.01)

(58) Field of Classification Search
USPC .................................................. 252/299.63
See application file for complete search history.

(56) References Cited

OTHER PUBLICATIONS

English translation of International Search Report dated Jan. 13, 2014; International Appl'n. No. PCT/CN2013/001416; International Filing Date: Nov. 19, 2013; 4 pages.

* cited by examiner

NEGATIVE DIELECTRIC ANISOTROPIC LIQUID CRYSTAL COMPOUNDS CONTAINING 2,3-DIFLUOROPHENYL GROUP, AND PREPARATION METHOD AND USE THEREOF

FIELD OF THE INVENTION

The present invention relates to the field of liquid crystal compounds, and more particularly, relates to a negative dielectric anisotropic liquid crystal compound containing 2,3-difluorophenyl, and a preparation method and use thereof.

BACKGROUND OF THE INVENTION

Since liquid crystals were initially synthesized by the scientist Reinitzer from Austria in 1888, the liquid crystal industry had truly a development only in recent 30 more years. Due to the obvious advantages of liquid crystal display materials, such as low driving voltage, low power consumption, high reliability, mass information display, color display, flicker-free display, and flat-panel display, both liquid crystal monomers and liquid crystal display have experienced enormous developments. More than 10 thousands of liquid crystal materials are currently synthesized with the liquid crystal monomers. Among them, thousands of liquid crystal display materials are commonly used, which mainly include, classified on the basis of the characteristics of the central bridge bond and rings in the liquid crystal molecules, biphenyl type liquid crystals, phenylcyclohexane type liquid crystals, ester type liquid crystals, acetylene type liquid crystals, difluoromethoxy bridge type liquid crystals, ethane type liquid crystals, heterocyclic type liquid crystals, and so on. Also, the liquid crystal display has developed from TN and STN of small black and white screen before 30 years into current TN-TFT, VA-TFT, IPS-TFT, and PDLC etc of large color screen.

New display modes of liquid crystal display include essentially optically compensated bend (OCB) mode, in-plane switching (IPS) mode, vertical alignment (VA) mode, axially symmetric aligned micro-cell (ASM) mode, multi-domain twisted nematic mode, and others.

The various display modes have different liquid crystal cell designs and driving modes, and also different relative relationship between liquid crystal molecule director and glass substrate orientation. For the OCB and IPS modes, the liquid crystal molecule director is parallel to the glass substrate orientation. For the VA and ASM modes, the liquid crystal molecule director is perpendicular to the glass substrate orientation in the absence of an electrical field.

The liquid crystal molecules in the IPS mode of parallel alignment have a dielectric anisotropy (Δ∈) that may be positive or negative.

The liquid crystal molecules in the VA mode have a director that is perpendicular to the glass substrate orientation and is parallel to the direction of a vertical incident light in the presence of a zero field. When polarizers are orthogonal, a good dark state will be displayed. Therefore, the devices of such a display mode have a good contrast, and the liquid crystals used should have a negative dielectric anisotropy (Δ∈). The optical anisotropy (Δn) of the liquid crystals, the thickness (d) of the liquid crystal cell, and the wavelength (λ) of the incident light almost have no influence on the contrast. The response time of VA-type devices is much shorter than, i.e., about half of, that of twisted nematic type devices. Under the influence of an applied voltage, the devices in VA, electrically controlled birefringence (ECB), and twisted nematic modes mainly undergo bend, splay, and twist distortions of the liquid crystal molecules, respectively, and the response times thereof are inversely proportional to the bend, splay, and twist elastic constants, respectively. For the majority of the liquid crystals, generally the bend elastic constant is greater than the splay elastic constant, which in turn is greater than the twist elastic constant, which also accounts for the fast response of the VA-type devices.

In order to make the performances of the display devices more desirable, efforts are devoted to the development of novel liquid crystal compounds, such that the performances of the liquid crystal compounds and display devices are continuously improved.

SUMMARY OF THE INVENTION

An objective of the present invention is to provide a negative dielectric anisotropic liquid crystal compound containing 2,3-difluorophenyl, and a preparation method and use thereof.

DETAILED DESCRIPTION OF THE INVENTION

Figure 1:
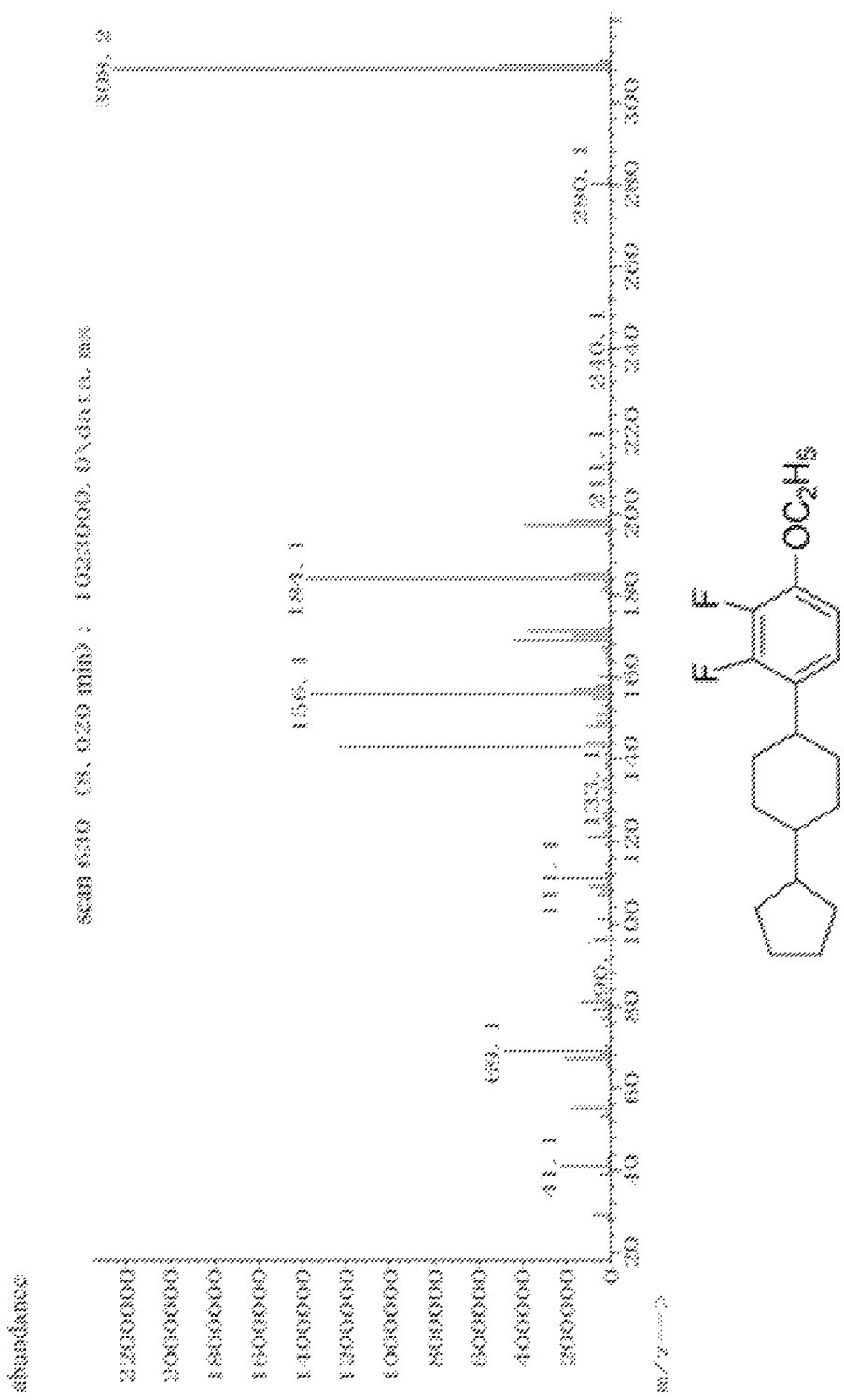
FIG. 1 is a mass spectrum of the product prepared in Example 1.

The negative dielectric anisotropic liquid crystal compound containing 2,3-difluorophenyl provided in the present invention has a general structural formula as shown in Formula I:

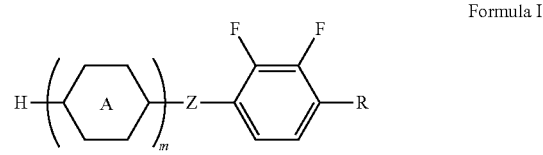

Formula I in which, H is cyclopentyl or cyclobutyl;

is selected from at least one of 1,4-phenylene, 1,4-phenylene substituted with fluoro, 1,4-cyclohexyl and 1,4-cyclohexyl in which one or two —$CH_2$— is substituted with O;

Z is selected from at least one of a single bond, —COO—, —$CH_2O$—, and —$CH_2CH_2$—;

R is selected from at least one of C1-C6 alkyl or C1-C6 alkoxy; particularly, C1-C5 alkyl, C1-C4 alkyl, C1-C3 alkyl, C1-C2 alkyl, C2-C5 alkyl, C2-C4 alkyl, C2-C3 alkyl, C3-C5 alkyl, C3-C4 alkyl, C4-C5 alkyl, C1-C5 alkoxy, C1-C4 alkoxy, C1-C3 alkoxy, C1-C2 alkoxy, C2-C5 alkoxy, C2-C4 alkoxy, C2-C3 alkoxy, C3-C5 alkoxy, C3-C4 alkoxy, or C4-C5 alkoxy, and more particularly, —OC$_2$H$_5$, —OC$_4$H$_9$, —CH$_3$, —C$_2$H$_5$, —C$_4$H$_9$, —OC$_3$H$_7$, or —OCH$_3$;

m is 1 or 2.

Specifically, the compound of Formula I is a compound of Formula Ia;

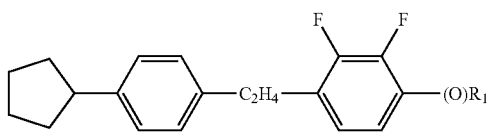

Formula Ia in which, H is cyclopentyl,

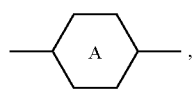

Z, R, and m are as defined above.

More specifically, the compound of Formula Ia is any one of the compounds of Formulas I1 to I9 below;

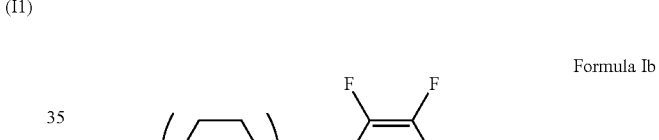

(I1)

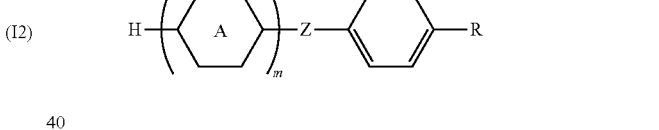

(I2)

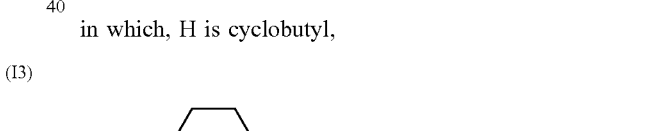

(I3)

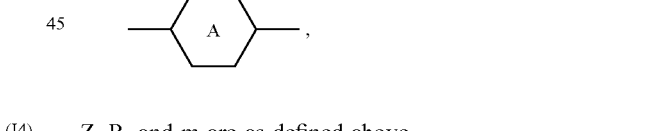

(I4)

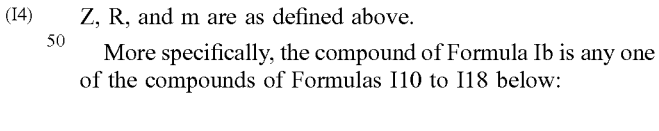

(I5)

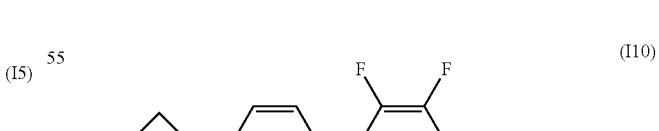

(I6)

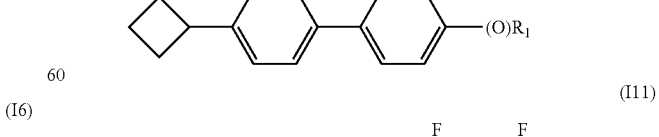

(I7)

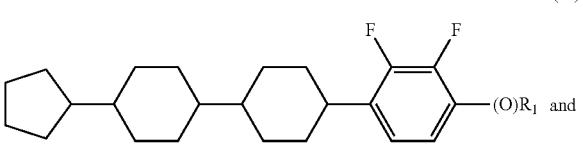

(I8)

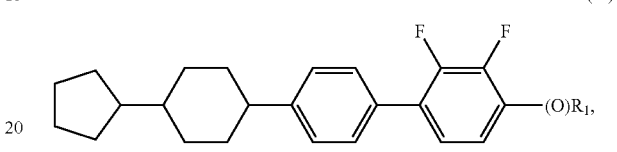

and (I9)

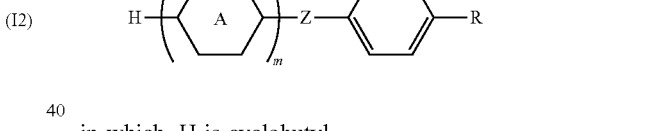

in which, R$_1$ is C1-C6 alkyl, particularly C1-C5 alkyl, C1-C4 alkyl, C1-C3 alkyl, C1-C2 alkyl C2-C5 alkyl, C2-C4 alkyl, C2-C3 alkyl, C3-C5 alkyl, C3-C4 alkyl or C4-C5 alkyl, and more particularly —C$_2$H$_5$, —C$_4$H$_9$, —C$_3$H$_7$ or —CH$_3$.

Specifically, the compound of Formula I is a compound of Formula Ib:

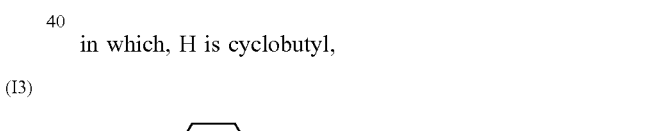

Formula Ib in which, H is cyclobutyl,

Z, R, and m are as defined above.

More specifically, the compound of Formula Ib is any one of the compounds of Formulas I10 to I18 below:

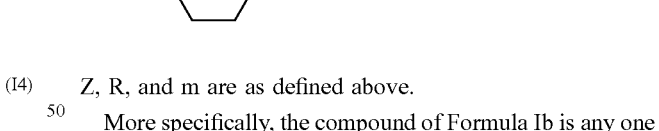

(I10)

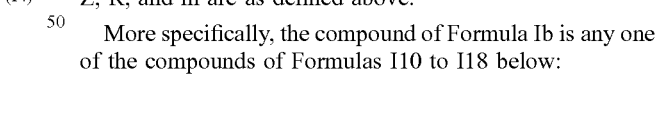

(I11)

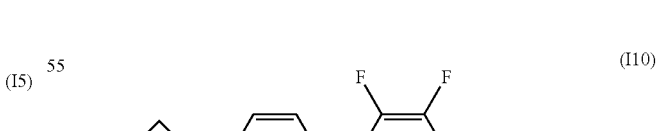

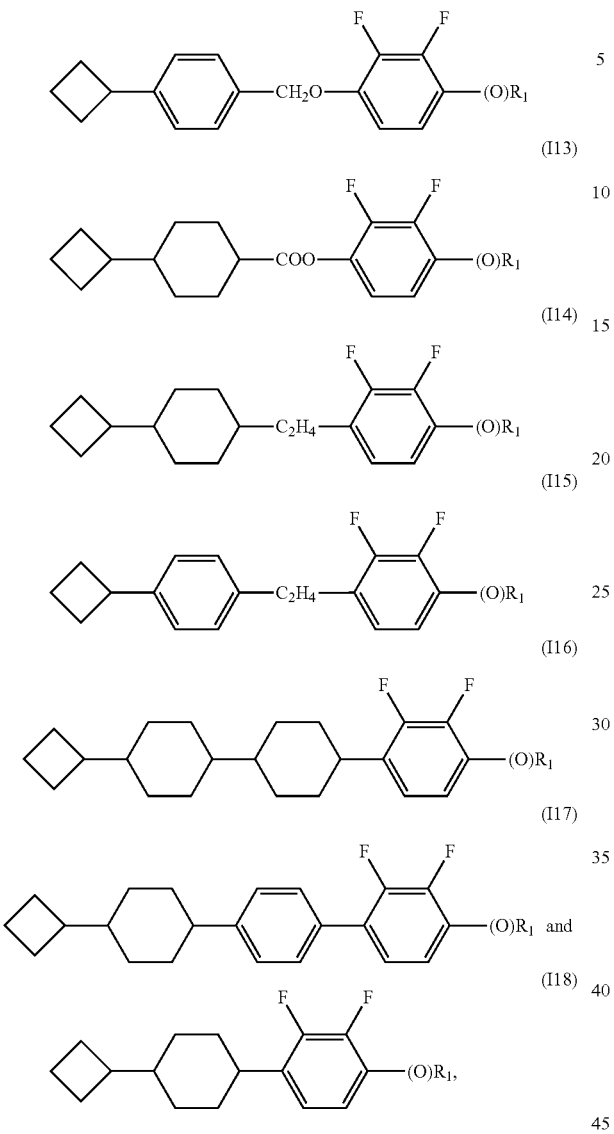

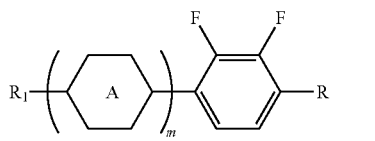

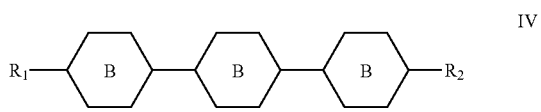

in which the weight ratio of the compounds of Formula II and III 5-50:50-95, and preferably 5-40:60-95; and
the component B2 comprises the compounds of Formulas II, III, and IV:

$$R_1 \text{—} B \text{—} B \text{—} B \text{—} R_2 \quad \text{IV}$$

in which the weight ratio of the compounds of Formulas II, III, and IV is 5-50:50-95:1-5, and preferably 5-40; 60-95:1-5.

In Formulas II to IV, $R_1$ is selected from at least one of C1-C6 alkyl or C1-C6 alkoxy, particularly C1-C5 alkyl, C1-C4 alkyl, C1-C3 alkyl, C1-C2 alkyl, C2-C5 alkyl, C2-C4 alkyl, C2-C3 alkyl, C3-C5 alkyl, C3-C4 alkyl, C4-C5 alkyl, C1-C5 alkoxy, C1-C4 alkoxy, C1-C3 alkoxy, C1-C2 alkoxy, C2-C5 alkoxy, C2-C4 alkoxy, C2-C3 alkoxy, C3-C5 alkoxy, C3-C4 alkoxy, or C4-C5 alkoxy, and more particularly —$OC_2H_5$, —$OC_4H_9$, —$CH_3$, —$C_2H_5$, —$C_4H_9$, —$OC_3H_7$, —$C_3H_7$ or —$OCH_3$.

$R_2$ is selected from at least one of C1-C6 alkyl or C2-C6 alkenyl, particularly C1-C5 alkyl, C1-C4 alkyl, C1-C3 alkyl, C1-C2 alkyl, C2-C5 alkyl, C2-C4 alkyl, C2-C3 alkyl, C3-C5 alkyl, C3-C4 alkyl, C4-C5 alkyl, C2-C5 alkenyl, C2-C4 alkenyl, C2-C3 alkenyl, C2-C5 alkenyl, C2-C4 alkenyl, C2-C3 alkenyl, C3-C5 alkenyl, C3-C4 alkenyl, or C4-C5 alkenyl, and more particularly —$C2H_3$, —$C_4H_7$, —$C_2H_3$, —$C_3H_3$, —$C_3H_7$, —$C_4H_9$ or —$CH_3$;

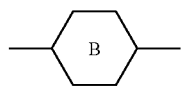

is 1,4-phenylene or 1,4-phenylene substituted with fluoro, and R,

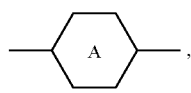

and m are as defined above.

in which, $R_1$ is C1-C6 alkyl, particularly C1-C5 alkyl, C1-C4 alkyl, C1-C3 alkyl, C1-C2 alkyl, C2-C5 alkyl, C2-C4 alkyl, C2-C3 alkyl, C3-C5 alkyl, C3-C4 alkyl, or C4-C5 alkyl, and more particularly —$C_2H_5$, —$C_4H_9$, —$C_3H_7$ or —$CH_3$.

Furthermore, the liquid crystal mixtures below also fall within the protection scope of the present invention:
a liquid crystal mixture 1 composed of a component A and a component B, in which the component A comprises at least one of the compounds of formula I;
a liquid crystal mixture II composed of a component Aa and a component B, in which the component Aa comprises at least one of the compounds of Formula Ia; and
a liquid crystal mixture III composed of a component Ab and a component B, in which the component Ab comprises at least one of the compounds of Formula Ib;
where the component B is a component B1 or B2:
the component B1 comprises the compounds of Formulas II and III:

For the liquid crystal mixtures I to III, any one of the compounds of Formula I in the component A, any one of the compounds of Formula Ia in the component Aa, or any one of the compounds of Formula Ib in the component Ab is present in the liquid crystal mixture in an amount of 1-30%, preferably 5-20%, and particularly 8-13%, 13%, or 8% by weight.

The component A, the component Aa, or the component Ab is present in an amount of 1-60%, preferably 5-40%, and more particularly 10-40%, 10%, 40%, 20-30%, 21%, 30%, 21-30%, 21-40% or 40% based on the total weight of the liquid crystal mixture.

Specifically, the liquid crystal mixture is a liquid crystal mixture a, b, c, d1, d2, e1, e2, f1, f2, g1 or g2.

The mentioned liquid crystal mixtures are all composed of the component A and the component B.

In the liquid crystal mixture a, the component A comprises 5-20 parts by weight of

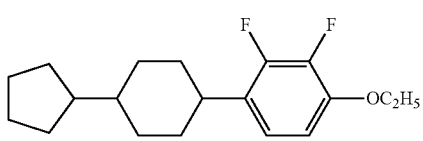

and 5-15 parts by weight of

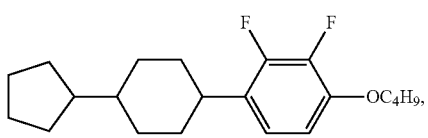

and the component A specifically comprises 17 parts by weight of

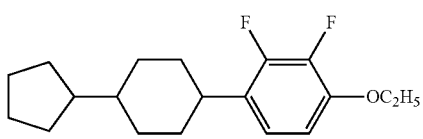

and 10 parts by weight of

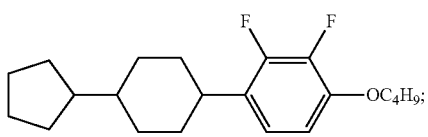

and
the component B is present in an amount of 100 parts by weight, and the component B specifically comprises, in parts by weight:

30
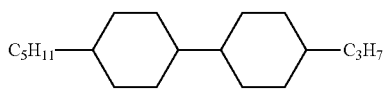

14
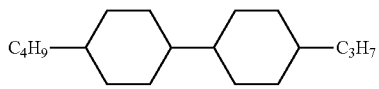

-continued

11
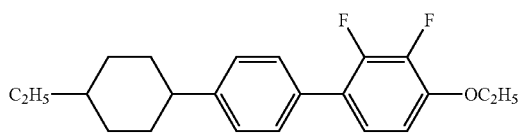

10
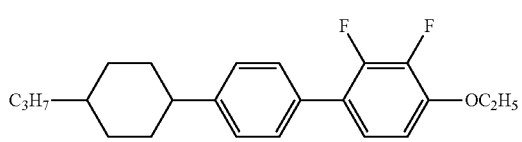

15
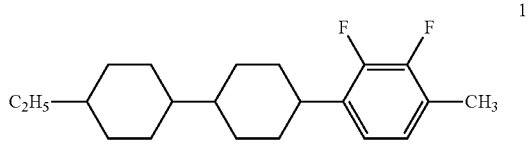

14
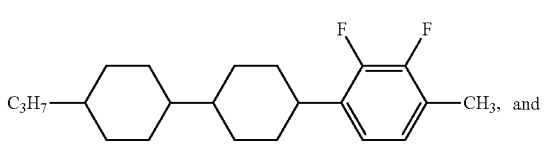, and

6
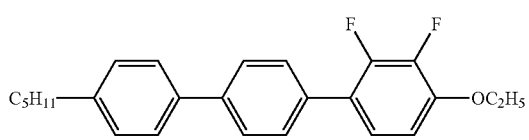

In the liquid crystal mixture b, the component A comprises 5-20 parts by weight of

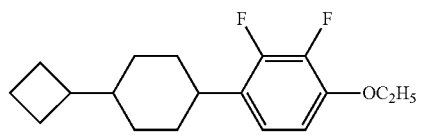

and 5-15 parts by weight of

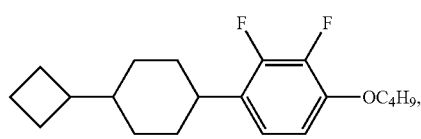

and the component A specifically comprises 17 parts by weight of

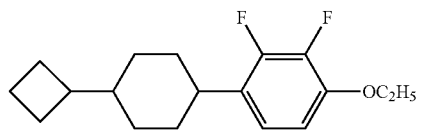

and 10 parts by weight of

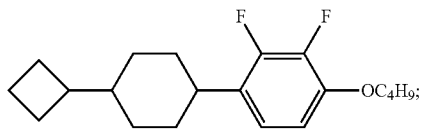

and the component B is the component B in the liquid crystal mixture a, and present in an amount of 100 parts by weight.

In the liquid crystal mixture c, the component A comprises 5-20 parts by weight of

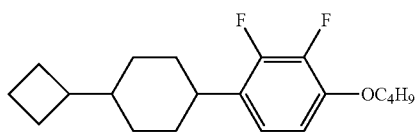

and 5-15 parts by weight of

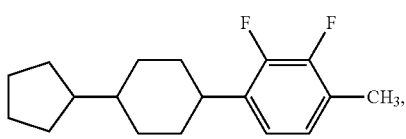 [SMILES: Cc1ccc(C2CCC(C3CCCC3)CC2)c(F)c1F]

and the component A specifically comprises 17 parts by weight of

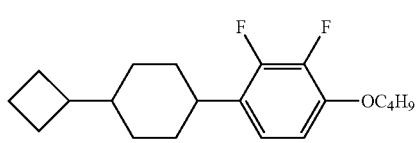

and 10 parts by weight of

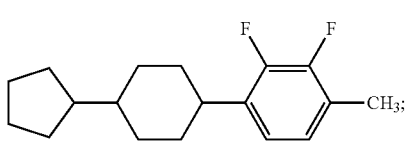

and the component B is the component B in the liquid crystal mixture a, and is present in an amount of 100 parts by weight.

In the liquid crystal mixture d1, the component A comprises 5-30 and specifically 27 parts by weight of

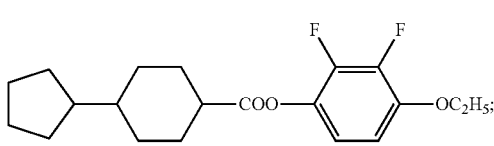

and the component B is the component B in the liquid crystal mixture a, and is present in an amount of 100 parts by weight.

In the liquid crystal mixture d2, the component A comprises 5-30 and specifically 27 parts by weight of

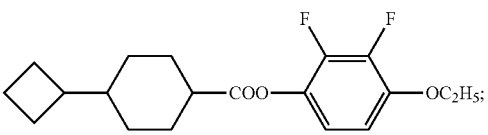

and the component B is the component B in the liquid crystal mixture a, and is present in an amount of 100 parts by weight.

In the liquid crystal mixture e1, the component A comprises 5-30 and specifically 27 parts by weight of

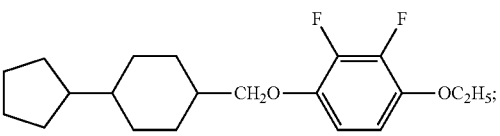

and the component B is the component B in the liquid crystal mixture a, and is present in an amount of 100 parts by weight.

In the liquid crystal mixture e2, the component A comprises 5-30 and specifically 27 parts by weight of

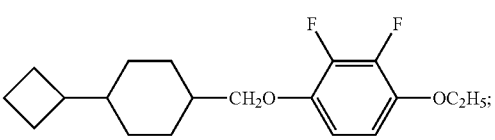

and the component B is the component B in the liquid crystal mixture a, and is present in an amount of 100 parts by weight.

In the liquid crystal mixture f1, the component A comprises 5-30 and specifically 27 parts by weight of

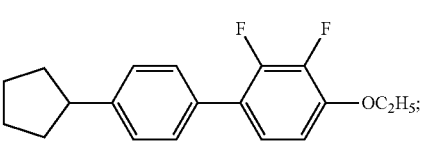 [SMILES: CCOc1ccc(-c2ccc(C3CCCC3)cc2)c(F)c1F]

and the component 8 is the component B in the liquid crystal mixture a, and is present in an amount of 100 parts by weight.

In the liquid crystal mixture f2, the component A comprises 5-30 and specifically 27 parts by weight of

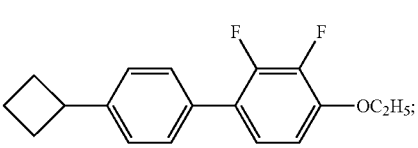 [SMILES: CCOc1ccc(-c2ccc(C3CCC3)cc2)c(F)c1F]

and the component B is the component B in the liquid crystal mixture a, and is present in an amount of 100 parts by weight.

In the liquid crystal mixture g1, the component A comprises 5-30 and specifically 27 parts by weight of

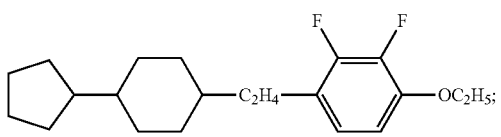

and the component B is the component B in the liquid crystal mixture a, and is present in an amount of 100 parts by weight.

In the liquid crystal mixture g2, the component A comprises 5-30 and specifically 27 parts by weight of

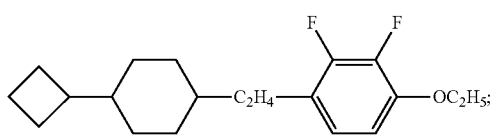

and the component B is the component B in the liquid crystal mixture a, and is present in an amount of 100 parts by weight.

Use of the compound of Formula I, the compound of Formula Ia, the compound of Formula Ib, or the liquid crystal mixture provided in the present invention in preparation of liquid crystal display materials or electrooptical display materials, and a liquid crystal display material or electrooptical liquid crystal display comprising the compound of Formula I, the compound of Formula Ia, the compound of Formula Ib, or the liquid crystal mixture also fall within the protection scope of the present invention. The electrooptical liquid crystal display is a VA, IPS, PS-VA, PSA-VA, PS-IPS or PSA-IPS display.

Use of the compound of Formula I, the compound of Formula Ia, the compound of Formula Ib, or the liquid crystal mixture provided in the present invention in adjustment of the clearing point and/or negative dielectric constant of a liquid crystal mixture also falls within the protection scope of the present invention. The adjustment of the clearing point of the liquid crystal mixture is to increase the clearing point of the liquid crystal mixture; and the adjustment of the negative dielectric constant of the liquid crystal mixture is to increase the absolute value of the negative dielectric constant of the liquid crystal mixture.

EXAMPLES

In the examples below, GC represents gas chromatographic purity, MP represents melting point, MS represents mass spectrometry, $\Delta\epsilon$ represents dielectric anisotropy, $\Delta n$ represents optical anisotropy, and Cp represents clearing point. The clearing point may be directly determined, and for a compound for which the clearing point cannot be directly determined, fitted data is calculated following the method below.

In the formulation of a mixed liquid crystal, numerous suitable monomer liquid crystals may be mixed to form an eutectic mixture, thereby effectively lowering the melting point of the mixed liquid crystal. In addition, a monomer liquid crystal with a high clearing point may be added to increase the clearing point of the mixed liquid crystal, thereby formulating a mixed liquid crystal with a nematic phase over a satisfactory temperature range. The clearing point of the mixed liquid crystal, and the clearing point and contents of the monomer liquid crystals meet the following relationship:

$Tc=\Sigma X_i T_i$ where, Tc represents the clearing point of the mixed liquid crystal, $X_i$ represents the content of the monomer liquid crystals present in the mixed liquid crystal, and $T_i$ represents the clearing point of the monomer liquid crystals.

Based on this, in case that the concentration of all monomer liquid crystals in the mixed liquid crystal, and the clearing points of other monomer liquid crystals are known, the clearing point of an monomer liquid crystal unknown in the examples below may be calculated following the equation above. The structural formulas and corresponding contents in parts by weight of the other monomer liquid crystals are shown below (the content of the unknown monomer liquid crystal is 4 parts by weight):

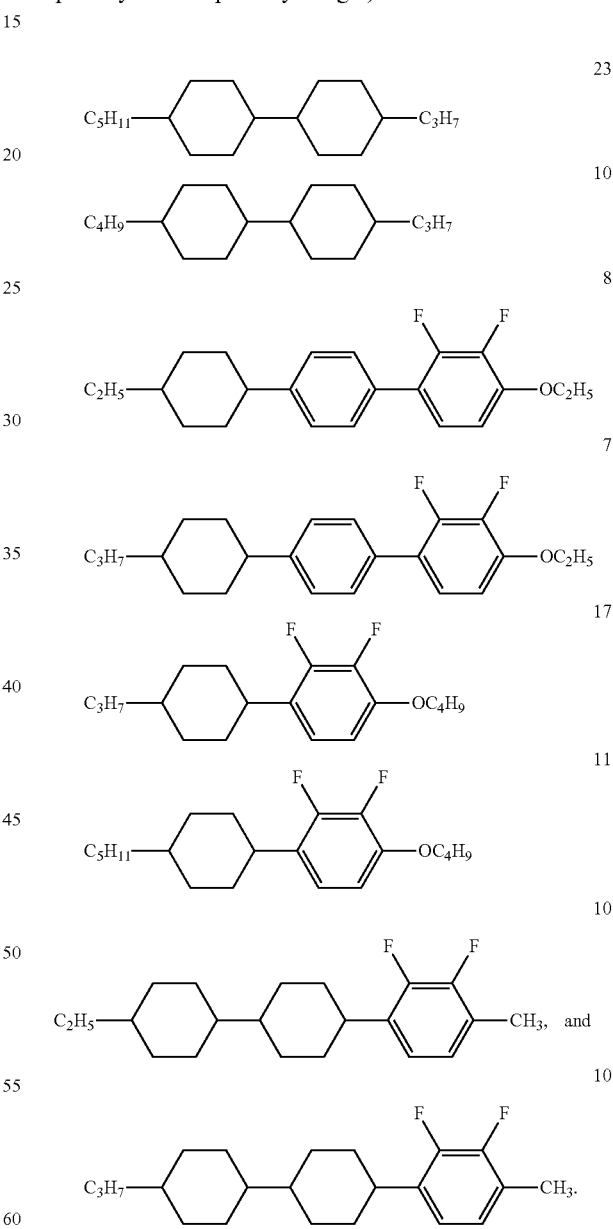

The compound of Formula I above is prepared as shown in Synthesis Routes 1 to 5. In Synthesis Routes 1 to 3, the synthesis of some intermediates that are not commercially available is given, and the synthesis principles, operations, conventional post treatments, chromatography over a silica gel column, purification through recrystallization, and others are all known to persons of skill in the art. The target products can be absolutely obtained through the synthesis process described below.

The progression of the reaction process is generally monitored by TLC. The post treatments after reaction generally include water washing, extracting, combining the organic phases and then drying, evaporating off the solvent under reduced pressure, recrystallizing, and column chromatography. The present invention may be accomplished by those skilled in the art following the description below.

I. Synthesis Route 1

A compound of Formula I is prepared, where ring A is 1,4-cyclohexyl, Z is a single bond, and m is 1 or 2.

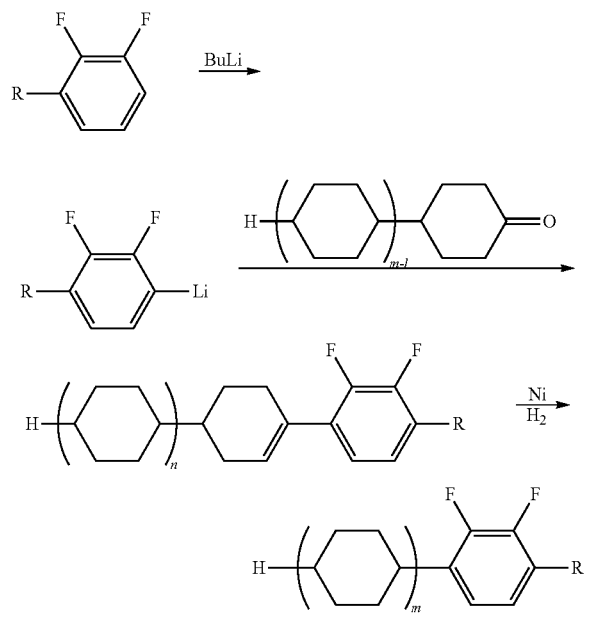

1) n-butyl lithium is added to a solution of

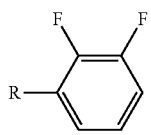

in the solvent tetrahydrofuran at −70° C. under an inert atmosphere, to perform substitution of

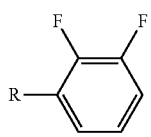

with lithium. After 15 min,

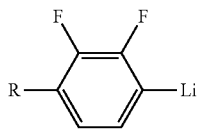

is obtained. Then

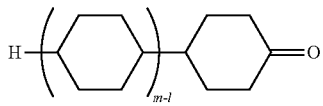

is added, to perform the addition of the lithium reagent onto the ketone. After addition, the solution is heated to −30° C., and then poured into 100 ml water. After phase separation, the organic phase is separated, washed 2 times with water, and directly evaporated to remove the solvent completely. The residue is added with p-toluene sulfonic acid and toluene, and water is removed under reflux until no water is separated out after 1 hr. Then, it is purified by silica gel column chromatography and after rinsing with petroleum ether and evaporation off of the solvent,

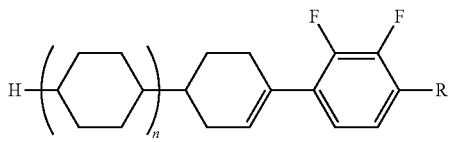

is obtained (n is 0 or 1).

2) The

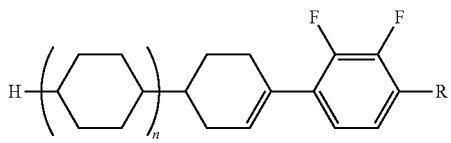

obtained in Step 1) is dissolved in toluene and ethanol, and hydrogenated at normal temperature under normal pressure for 10 hrs in the presence of the catalyst Raney nickel, to obtain a compound of Formula I, in which ring A is 1,4-cyclohexyl, Z is a single bond, and m is 1 or 2.

The intermediates

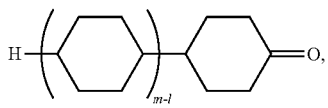

that is,

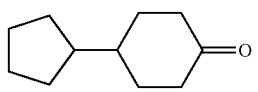

(1-a)

(correspondingly, H is cyclopentyl, and m is 1),

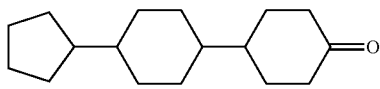
(1-b)

(correspondingly, H is cyclopentyl, and m is 2).

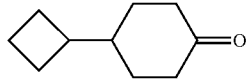
(1-c)

(correspondingly, H is cyclobutyl, and m is 1), and

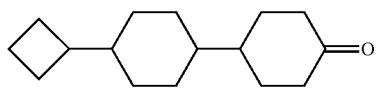
(1-d)

(correspondingly, H is cyclobutyl, and m is 2) are prepared as follows:

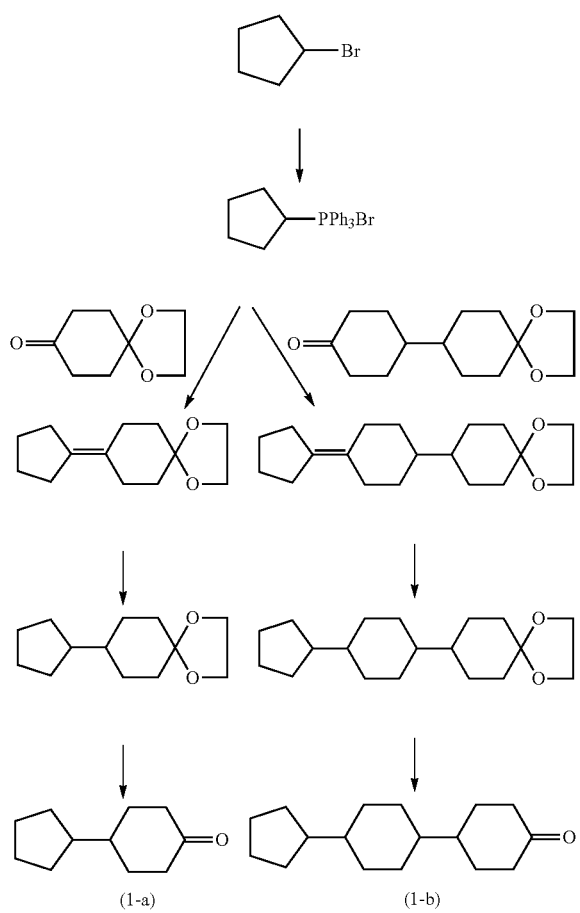

The synthesis process in the intermediate synthesis route 1 is described by means of an example in which bromocyclopentane is used as a starting material.

Bromocyclopentane and triphenylphosphine are directly heated to 110° C. for 6 hrs in the absence of a solvent and part of the unreacted raw material is dissolved in toluene, to obtain cyclopentyl triphenylphosphonium bromide. The resulting cyclopentyl triphenylphosphonium bromide is reacted with potassium tert-butoxide in the solvent tetrahydrofuran at 0° C. to generate the corresponding Ylide reagent, which undergoes Witting reaction with

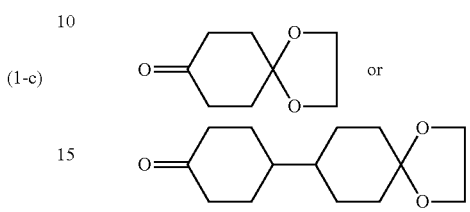

for 2-4 hrs. The solvent is directly removed by evaporation. The product intermediate alkene is extracted out with petroleum ether, which is hydrogenated in the solvent isopropanol in the presence of the catalyst Pd/C, with the alkene bond converted into a saturated bond. The trans-structured product is recovered through recrystallization in petroleum ether, and deprotected in the presence of formic acid in the solvent toluene at room temperature, to obtain

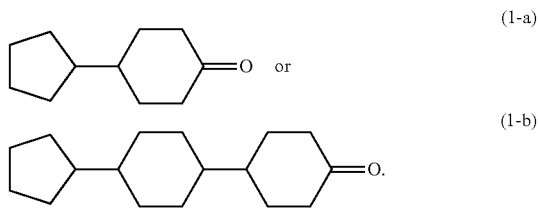
(1-a)
(1-b)

Following the same method, by substituting bromocyclobutane for bromocyclopentane,

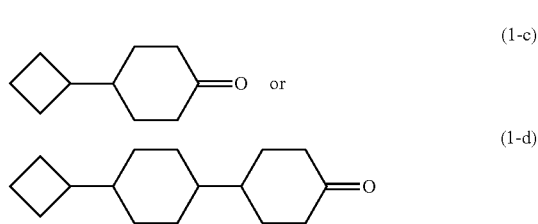
(1-c)
(1-d)

is obtained.

Mass spectrometry results of (1-a) and (1-b) are as follows: MS: m/z % 166 (M$^+$ 39) 137 (40) 125 (100) 69 (57.4); and MS; m/z % 24 (M$^+$ 84.4) 230 (26.5) 95 (100) 67 (72.9).

II. Synthesis Route 2

A compound of Formula I is prepared, where ring A is 1,4-cyclohexyl, Z is —COO—, and m is 1 or 2.

(2-b)
(2-c)
+
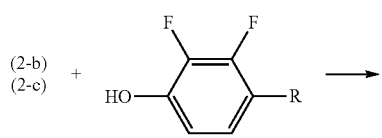

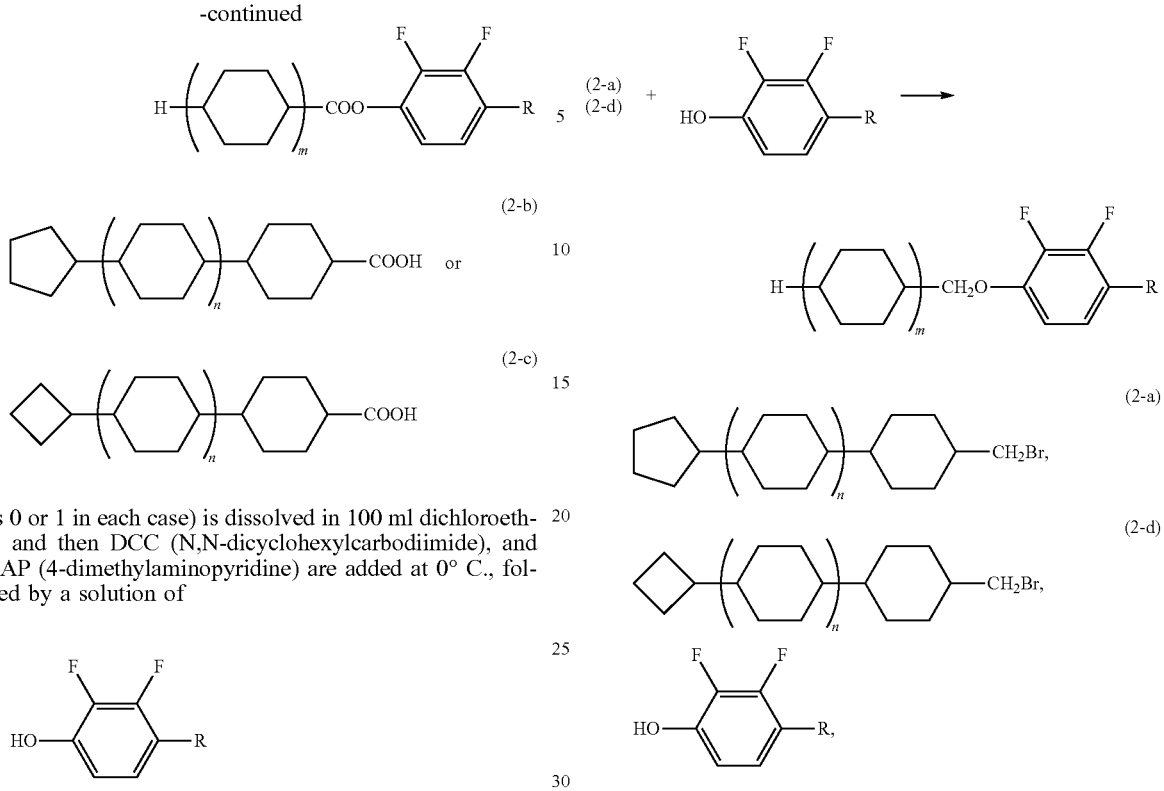

(n is 0 or 1 in each case) is dissolved in 100 ml dichloroethane, and then DCC (N,N-dicyclohexylcarbodiimide), and DMAP (4-dimethylaminopyridine) are added at 0° C., followed by a solution of in dichloroethane, then subjected to esterification for 4 hrs with stirring at room temperature, and filtered to remove the precipitated by-product DCU. The filtrate is evaporated under reduced pressure to completely remove the solvent. The residue is dissolved in petroleum ether, purified by silica gel column chromatography, evaporated again under reduced pressure to completely remove the solvent, and then recrystallized in 100 ml ethanol (3×), to obtain a compound of formula I in which ring A is 1,4-cyclohexyl, Z is —COO—, and m is 1 or 2.

III. Synthesis Route 3

A compound of Formula I is prepared, where ring A is 1,4-cyclohexyl, Z is —CH$_2$O—, and m is 1 or 2.

potassium carbonate, and the solvent ethanol are uniformly mixed and heated to reflux with stirring, to generate a potassium phenoxide. A solution of 2-a or 2-d (n is 0 or 1 in each case) in ethanol is added dropwise, and then etherificated for 4 hrs under reflux. The reaction solution is poured into water and extracted with diethyl ether. The organic phase is washed with water, evaporated to remove the solvent completely, dissolved in petroleum ether, purified by silica gel column chromatography, further evaporated to remove the solvent completely, and then recrystallized in ethanol, to obtain a compound of Formula I in which ring A is 1,4-cyclohexyl, Z is —CH$_2$O—, and m is 1 or 2.

In Synthesis Routes 2 and 3, the intermediates 2-a, 2-b, 2-c, and 2-d used are prepared, as follows:

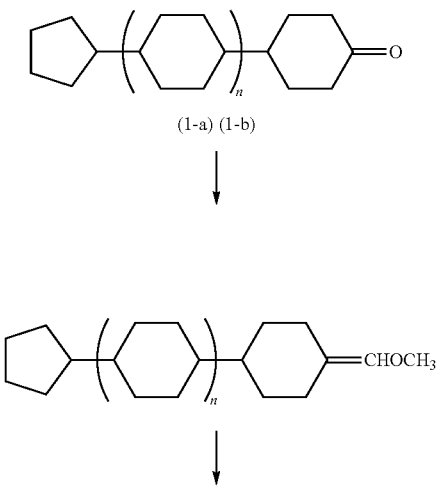

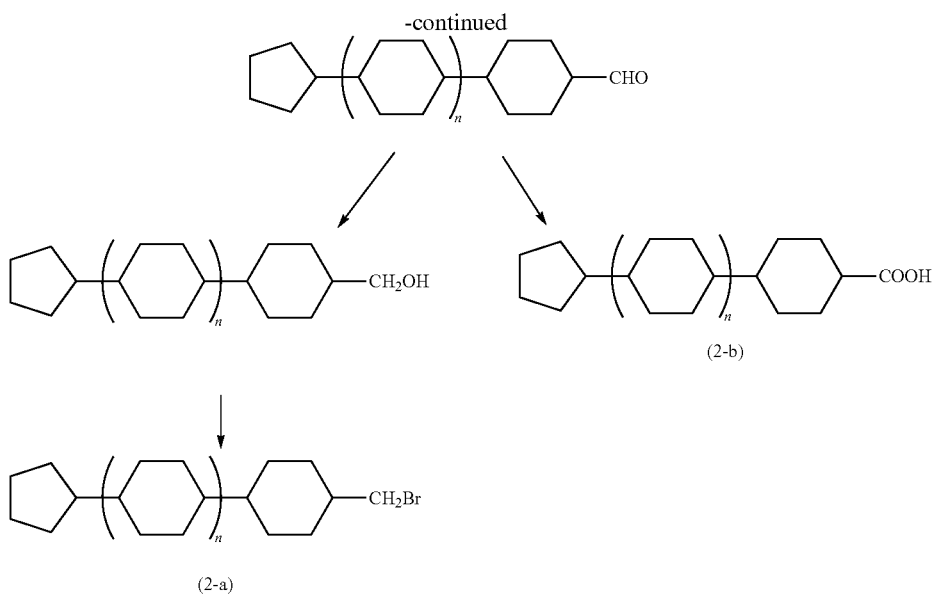

(2-b)

(2-a)

Following the same method, by substituting bromocyclobutane for bromocyclopentane,

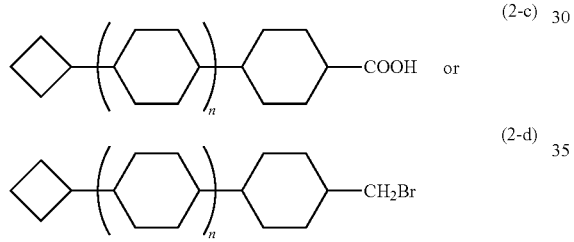

is obtained.

The preparation method above is specifically as follows.

1) Methoxymethylphosphonium chloride is reacted with potassium tert-butoxide in tetrahydrofuran at about 10° C. to generate the corresponding Ylide reagent, which undergoes Witting reaction with (1-a), (1-b), (1-c) or (1-d) for 2-4 hrs. The solvent is directly removed by evaporation. The product intermediate alkene is extracted out with petroleum ether, and hydrolyzed in 2 N dilute hydrochloric acid, to obtain the corresponding aldehyde. The cyclohexane attached to the formyl group has cis-trans isomerism. The trans-structured product aldehyde is recovered through recrystallization in petroleum ether. The trans-structured product aldehyde is oxidized to obtain an acid.

2) Reduction: the trans-structured product aldehyde is dissolved in tetrahydrofuran, and then an aqueous potassium borohydride solution is added dropwise at 0° C., and reacted for an additional 4 hrs after addition. Water is added, and the product is extracted out with diethyl ether, to obtain an alcohol.

3) Bromination: the alcohol is stirred with ½ mole of phosphorus tribromide overnight at 40° C., hydrolyzed, extracted with diethyl ether, and recrystallized in petroleum ether to obtain a bromide (2-a), (2-d).

4) Oxidation: the trans-structured product aldehyde is dissolved in acetic acid, and then 15% hydrogen peroxide is added dropwise, and reacted for an additional 4 hrs after addition. The reaction solution is diluted with water, and then the solid is filtered, and recrystallized in petroleum ether to obtain an acid (2-b), (2-c).

DSC of

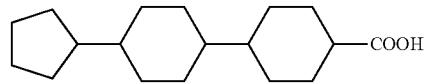 [SMILES: O=C(O)C1CCC(C2CCC(C3CCCC3)CC2)CC1]

is 145-155° C.; DSC of

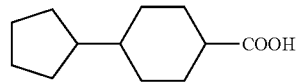 [SMILES: O=C(O)C1CCC(C2CCCC2)CC1]

is 63.7-66.2° C. 161.1-163.4° C. Mass spectrometry results thereof: MS: m/z % 196 (M$^+$ 17.6) 178 (37.2) 127 (38.6) 109 (66.1) 81 (100) 67 (44.8).

IV. Synthesis Route 4

A compound of Formula I is prepared, where ring A attached to Z is 1,4-phenylene or 1,4-phenylene substituted with fluoro, Z is a single bond, and m is 1 or 2.

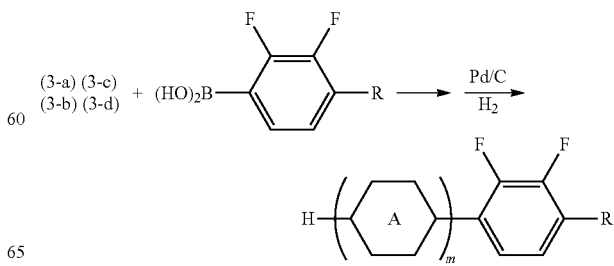

1)

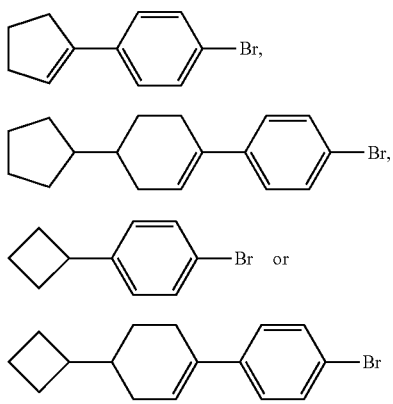

is uniformly mixed with

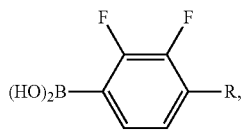

sodium carbonate, toluene, ethanol, water and tetrakis(triphenylphosphine) palladium, heated to reflux with stirring for SUZUKI reaction for 5 hrs. Then water is added and the organic phase is separated. The aqueous phase is extracted with toluene (1×). The organic phases are combined, washed 2 times with water, evaporated to completely remove the solvent, dissolved in petroleum ether, purified by silica gel column chromatography, and then recrystallized in petroleum ether, to obtain an intermediate.

2) The intermediate obtained in Step 1) is dissolved in toluene and ethanol, and hydrogenated for 8 hrs under normal pressure in the presence of Pd/C until the theoretical hydrogen absorption is attained. Then the Pd/C was filtered off, and the filtrate was evaporated under reduced pressure to remove the solvent, dissolved in petroleum ether, purified by silica gel column chromatography, and then recrystallized in petroleum ether, to obtain a compound of Formula I in which ring A attached to Z is 1,4-phenylene or 1,4-phenylene substituted with fluoro, Z is a single bond, and m is 1 or 2.

The intermediates

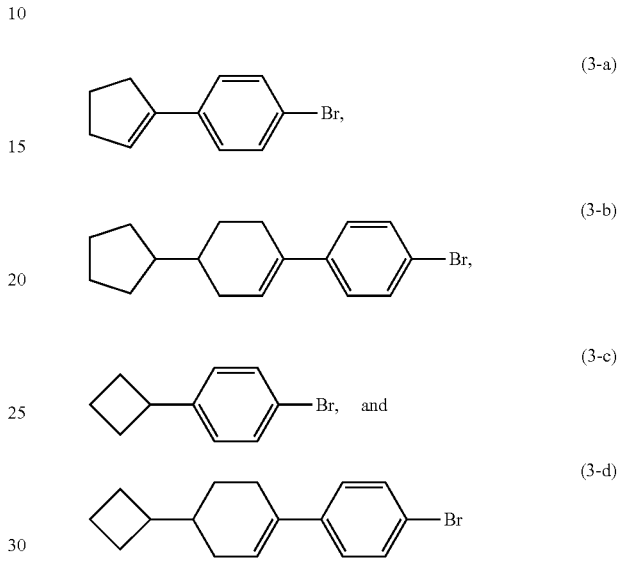

are prepared as follows:

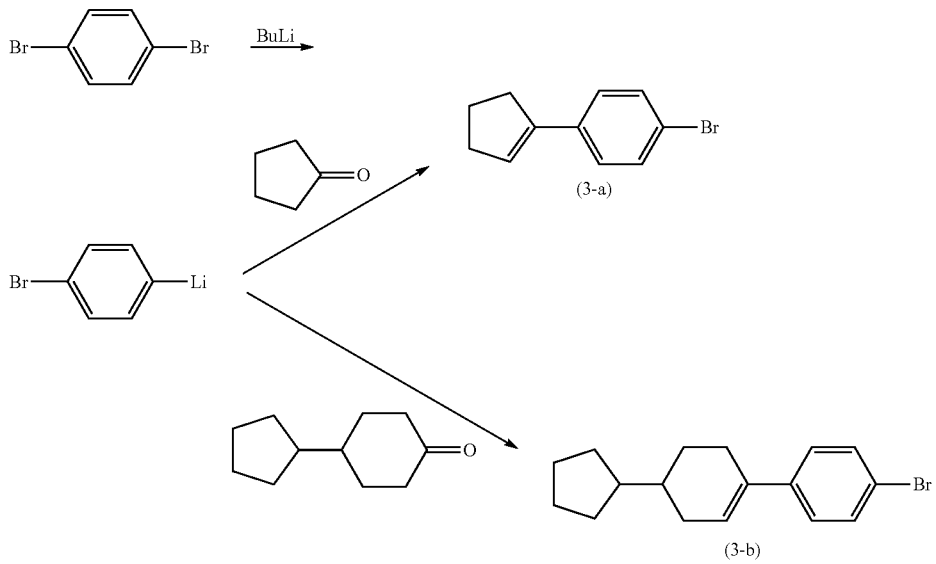

1,4-dibromobenzene is dissolved in tetrahydrofuran, then n-butyl lithium is added dropwise at −70° C., and then cyclopentanone, 4-cyclopentylcyclohexanone (1-a) or 4-cyclobutylcyclohexanone (1-c) is added dropwise 0.5 hr later, and hydrolyzed for 1 hr after addition, extracted with diethyl ether, washed with water, evaporated to remove the solvent, dehydrated for 2 hrs in the solvent toluene in the presence of the catalyst p-toluene sulfonic acid, purified by silica gel column chromatography, and then recrystallized in petroleum ether, to obtain (3-a), (3-b) or

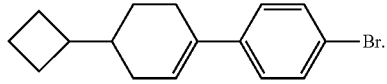 (3-d)

The method above is specifically as follows. 1,4-dibromobenzene is dissolved in tetrahydrofuran and n-butyl lithium is added dropwise at −70° C. and then cyclobutanone is added dropwise 0.5 hr later, hydrolyzed for 1 hr after addition, extracted with diethyl ether, washed with water, evaporated to remove the solvent, reacted in the solvent dichloromethane for 4 hrs at −70° C. with stirring in the presence of triethyl silicane and boron trifluoride etherate, hydrolyzed, extracted with diethyl ether, purified by silica gel column chromatography, recrystallized in petroleum ether, and then filtered at a low temperature to obtain

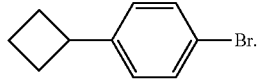 (3-c)

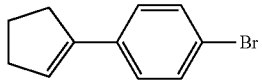 (3-a)

DSC: 98.7° C. MS: m/z % 222 (M⁺ 45.6) 143 (100) 128 (78.8) 115 (36.6).

V. Synthesis Route 5

A compound of Formula I is prepared, where ring A is 1,4-cyclohexyl, Z is —CH$_2$CH$_2$—, and m is 1 or 2.

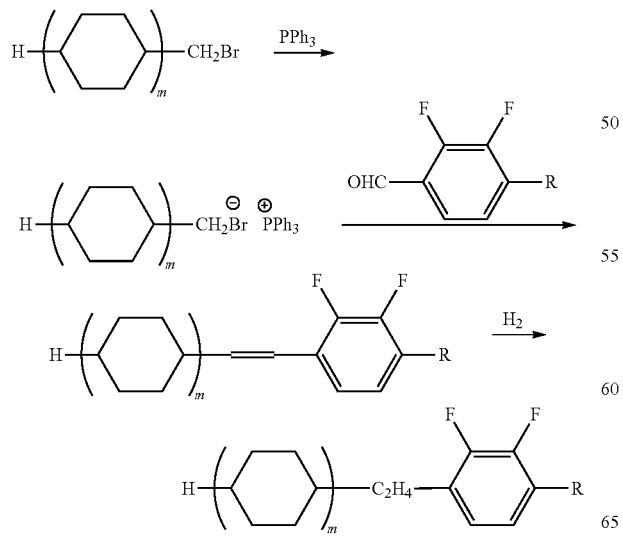

1)

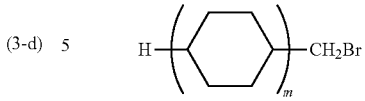

and triphenylphosphine are dissolved in toluene, heated to reflux for 6 hrs to form a salt, and then cooled to room temperature. The precipitated solid was filtered off, to obtain

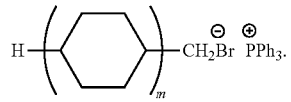

2)

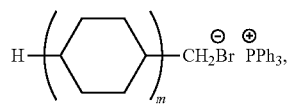

and tetrahydrofuran are cooled to −10° C., and then potassium tert-butoxide is added while the temperature is controlled below 0° C., to obtain a yellow solution. A solution of

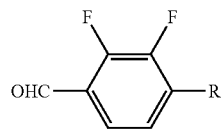

in tetrahydrofuran is added dropwise, and then subjected to Wittig reaction for 4 hrs. The reaction solution is poured into 400 ml water, and the organic phase is separated. The aqueous phase is extracted with 100 ml ethyl acetate (1×). The organic phases are combined, washed with water (1×), evaporated under reduced pressure to completely remove the solvent, extracted with petroleum ether (100 ml×4), purified by silica gel column chromatography, and then recrystallized in ethanol, to obtain

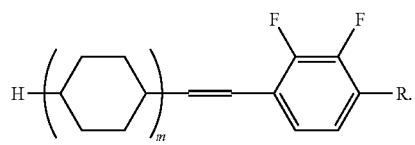

3) The

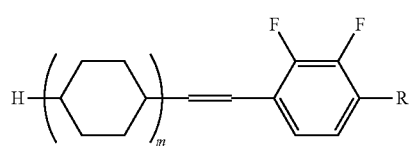

obtained in Step 2) is dissolved in toluene and ethanol, and hydrogenated for 6 hrs under normal pressure in the presence of Pd/C until the theoretical hydrogen absorption is attained. Then the Pd/C was filtered off, and the filtrate was purified by silica gel column chromatography, and then recrystallized in petroleum ether, to obtain a compound of Formula I in which ring A is 1,4-cyclohexyl, Z is —$CH_2CH_2$—, and m is 1 or 2.

Example 1

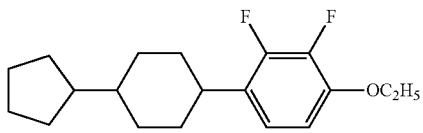

Step 1:

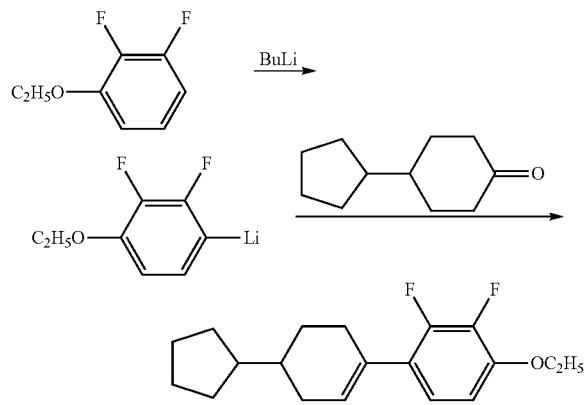

9.5 g (0.06 mol) 2,3-difluorophenetole and 80 ml tetrahydrofuran were added to a 250 ml three-neck flask, purged with nitrogen, and cooled to −70° C. 27 ml (2.5 M) (0.065 mol) n-butyl lithium was added dropwise over 15 min, and the solution was still colorless and transparent after addition. Then 9.5 g (0.057 mol) 4-cyclopentylcyclohexanone (1-a) was added dropwise, and the solution appeared light yellow after addition. The solution was naturally warmed to −30° C., and then poured into 100 ml water. After phase separation, the organic phase was separated, washed twice with water, and then directly evaporated to completely remove the solvent. The residue was added with 0.3 g p-toluene sulfonic acid, and 100 ml toluene, and water was removed under reflux until no water was separated out after 1 hr. Then, it was purified by silica gel column chromatography, rinsed with petroleum ether, and then evaporated to completely remove the solvent, to obtain 17 g of a solid, which was recrystallized in 50 ml ethanol, to obtain 10 g of a light yellow crystal. Yield: 57%, GC 99.1%.

Step 2:

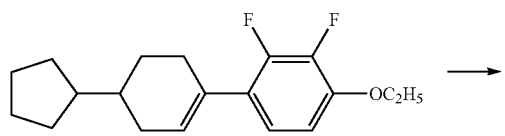

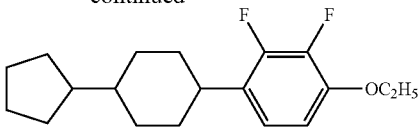

10 g of the product, that is, the light yellow crystal, obtained in Step 1 was dissolved in 20 ml toluene and 50 ml ethanol, added with 2 g of the catalyst Raney nickel, and hydrogenated for 10 hrs at normal temperature under normal pressure until the theoretical hydrogen absorption is attained. Then the catalyst Raney nickel was carefully filtered off, and the filtrate was evaporated to completely remove the solvent, dissolved in petroleum ether, purified by silica gel column chromatography, evaporated again to completely remove the solvent, recrystallized in ethanol at 10° C. (30 ml×3), to obtain a white crystal with a GC purity of 99.92%, MP: 77.7-79.6° C. MS: see FIG. 1. Δn [589 nm, 20° C.]: 0.082. Δ∈[KHz, 20° C.]: −5.6. Cp: fitted data 17° C.

Following the synthesis process in Example 1, the compounds below were synthesized with different raw materials, for which the structure characterization and performance parameters were as follows:

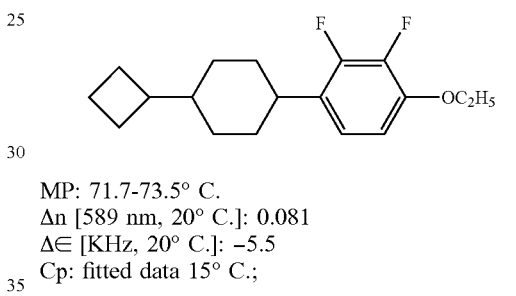

MP: 71.7-73.5° C.
Δn [589 nm, 20° C.]: 0.081
Δ∈ [KHz, 20° C.]: −5.5
Cp: fitted data 15° C.;

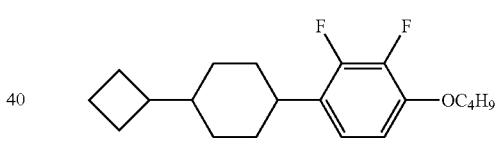

MP: 62.3-65.6° C.
Δn [589 nm, 20° C.]: 0.079
Δ∈[KHz, 20° C.]: −5.6
Cp: fitted data 14° C.

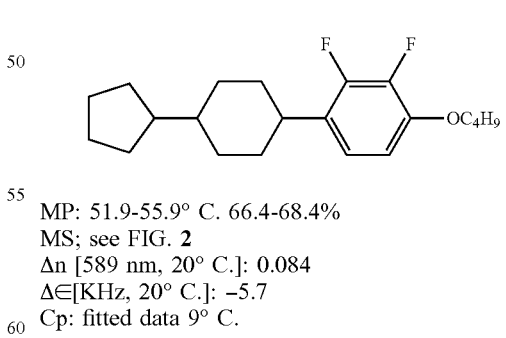

Figure 2:
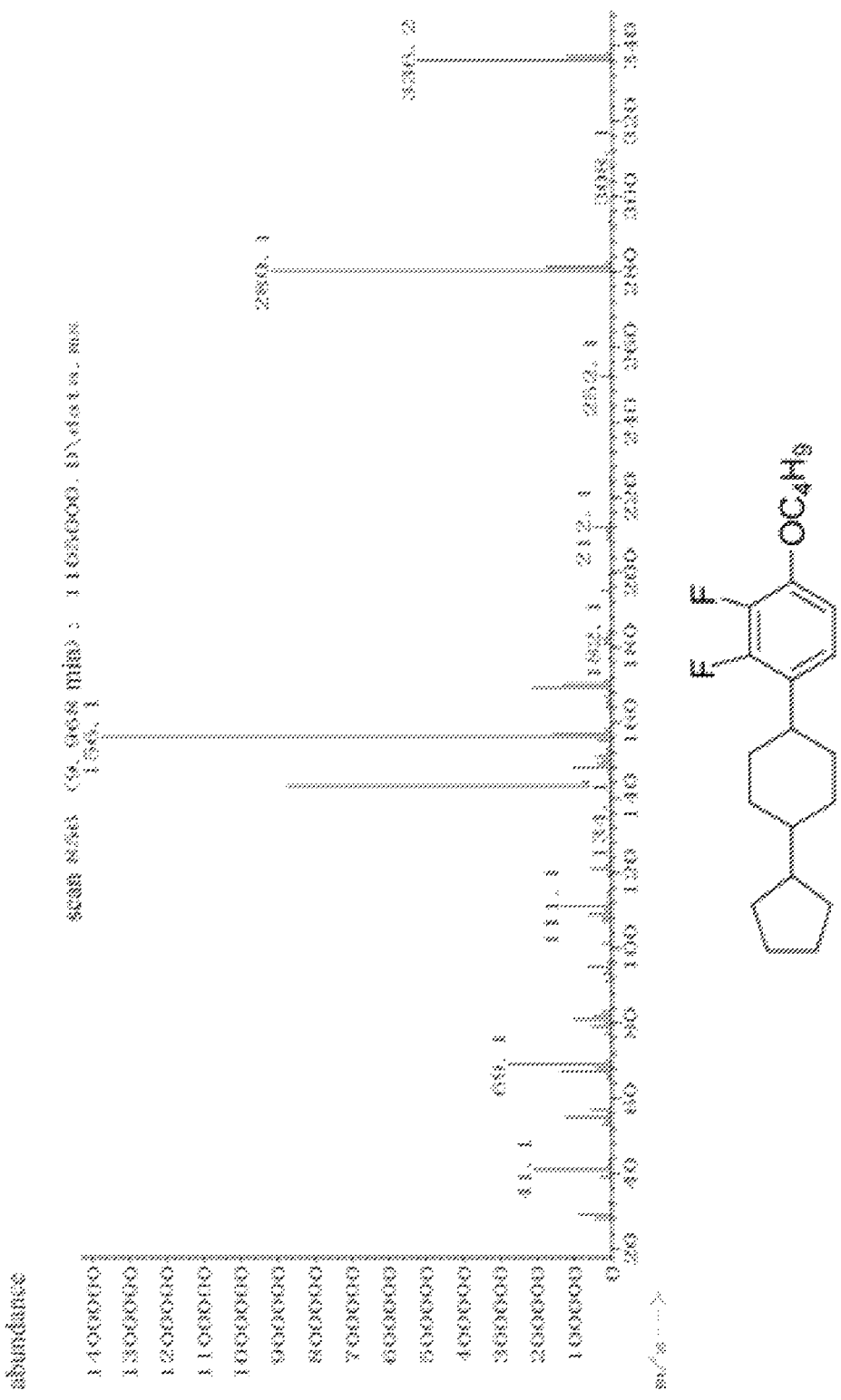
FIG. 2 is a mass spectrum of the product prepared in Example 1.

MP: 51.9-55.9° C. 66.4-68.4%
MS; see FIG. 2
Δn [589 nm, 20° C.]: 0.084
Δ∈[KHz, 20° C.]: −5.7
Cp: fitted data 9° C.

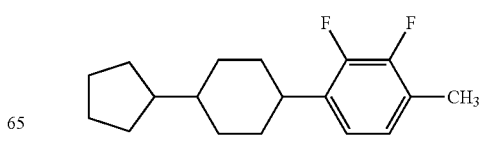

MP: 57.2-58.9° C.

MS: m/z % 278 (M⁺ 79.6) 167 (18) 154 (963) 141 (100) 127 (13.7)

Δn [589 nm, 20° C.]: 0.048

Δ∈[Khz, 20° C.]: −3.1

Cp: fitted data −5° C.

Example 2

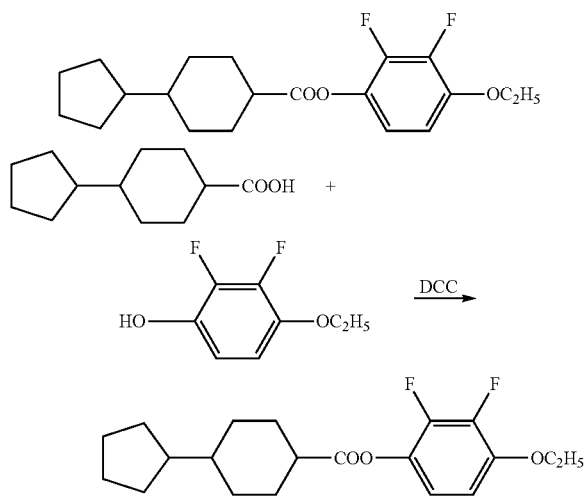

11.7 g (0.06 mol) 4-cyclopentylcyclohexylcarboxylic acid (2-b, n=0) was dissolved in 100 ml dichloroethane, 12.4 g (0.06 mol) DCC (N,N-diyclohexylcarbodiimide) and 0.1 g DMAP were added at 0° C., then a solution of 8.7 g (0.05 mol) 2,3-difluoro-4-ethoxyphenol in 20 ml dichloroethane was added dropwise, and then reacted for 4 hrs at room temperature with stirring. The precipitated by-product DCU was filtered off, and the filtrate was evaporated under reduced pressure to completely remove the solvent, dissolved in petroleum ether, purified by silica gel column chromatography, evaporated again under reduced pressure to completely remove the solvent, and recrystallized in ethanol (100 ml×3), to obtain 13.4 g of a white crystal with a Gc purity of 99.93%. Yield; 76%. MP: 82.1-84.6° C. MS: m/z % 352 (M⁺ 3.1) 179 (2.8) 174 (100) 146 (85.2), Δn [589 nm, 20° C.]: 0.097, Δ∈[KHz, 20° C.]: −6.4. Cp: fitted data 64.2° C.

Following the synthesis process in Example 2, the compounds below were synthesized with different raw materials, which had the following performance parameters:

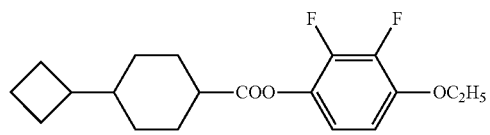

Δn [589 nm, 20° C.]: 0.094

Δ∈ [KHz, 20° C.]: −6.9

Cp: fitted data 65° C.

Example 3

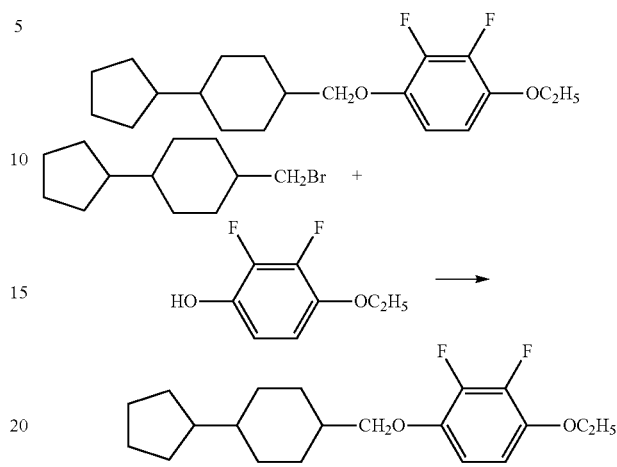

8.7 g (0.05 mol) 2,3-difluoro-4-ethoxyphenol, and 8.3 g (0.06 mol) potassium carbonate were charged to a 250 ml three-neck flask, and then 60 ml of the solvent ethanol was added, and heated to reflux with stirring. A solution of 13.8 g 4-cyclopentylcyclohexylmethyl bromide (2-a, n=0) in 30 ml ethanol was added dropwise, and then refluxed for another 4 hrs after addition. The reaction solution was poured into 200 ml water, and extracted with diethyl ether. The organic phase was washed with water, evaporated to completely remove the solvent, dissolved in petroleum ether, purified by silica gel column chromatography, evaporated again to completely remove the solvent and then recrystallized in 120 ml ethanol, to obtain 9.8 g of a white crystal. Gc: 99.90%. Yield: 58%. MP: 92.3-97.5° C., MS: m/z % 338 (M⁺ 5.6) 174 (100) 146 (37.2) 69 (4.9), Δn [589 nm, 20° C.]: 0.072. Δ∈[KHz, 20° C.]: −6.4. Cp: lined data 12.5° C.

Following the synthesis process in Example 3, the compounds below were synthesized with different raw materials, which had the following performance parameters;

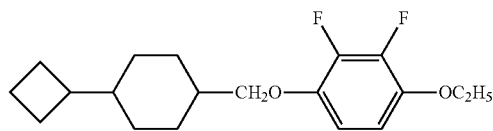

Δn [589 nm, 20° C.]: 0.070

Δ∈ [KHz, 20° C.]: −6.3

Cp: fitted data C6.8° C.

Example 4

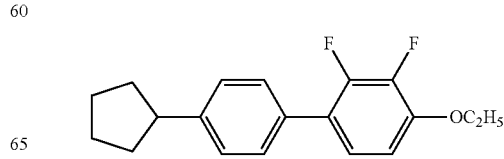

Step 1:

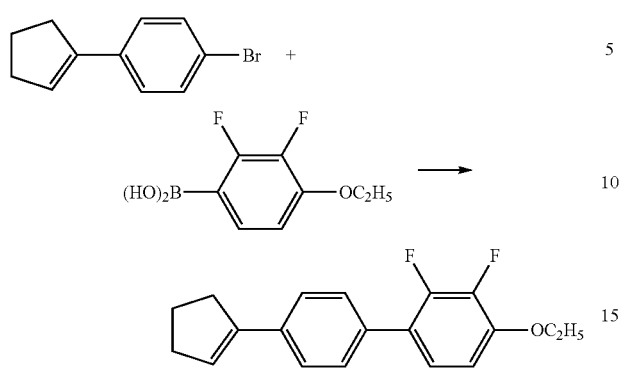

(4-a)

Under nitrogen atmosphere, 11.1 g (0.05 mol) 4-cyclopentenylphenyl bromide (3-a), 10.1 g (0.05 mol) 2,3-difluoro-4-ethoxyphenylboronic acid, 6.4 g (0.06 mol) sodium carbonate, 50 ml toluene, 50 ml ethanol, 50 ml water, and 0.3 g tetrakis(triphenylphosphine)palladium were charged together to a 250 ml three-neck flask, and heated to reflux for 5 hrs with stirring, 100 ml water was added, and the organic phase was separated. The aqueous phase was extracted with 20 ml toluene (1×). The organic phases were combined, washed twice with water, evaporated to completely remove the solvent, dissolved in petroleum ether, purified by silica gel column chromatography, and then recrystallized in petroleum ether, to obtain 12 g of a white crystal (4-a). Yield: 80%.

Step 2:

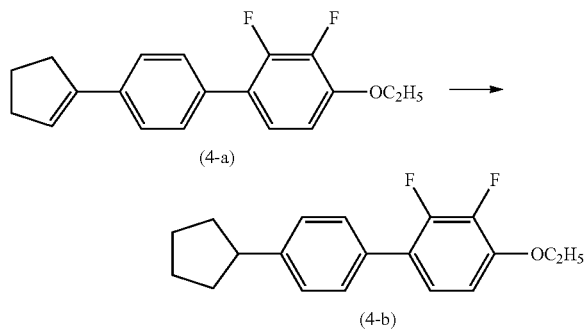

Figure 3:
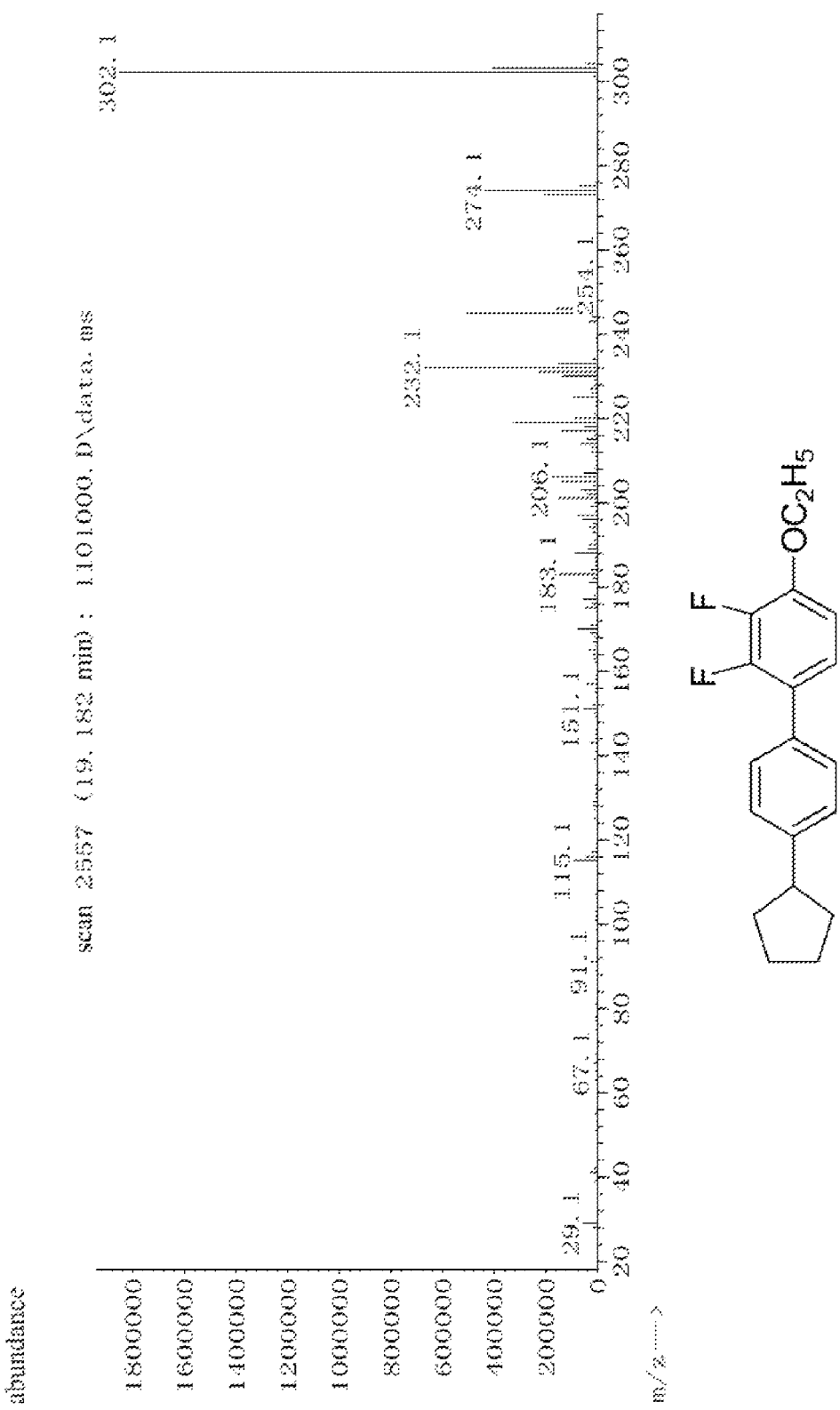
FIG. 3 is a mass spectrum of the product prepared in Example 4.

12 g of the white crystal (4-a) was dissolved in 50 ml toluene and 50 ml ethanol, added with 0.5 g Pd/C, and hydrogenated for 8 hrs under normal pressure until the theoretical hydrogen absorption is attained. Then the Pd/C was filtered off, and the filtrate was evaporated to remove the solvent, dissolved in petroleum ether, purified by silica gel column chromatography, and then re-crystallized in petroleum ether, to obtain 10.6 g of a white crystal with a Gc purity of 99.93%, Yield: 88%, MP: 98.7-100.7° C. MS: see FIG. 3. Δn [589 nm, 20° C.]: 0.153. Δ∈[KHz, 20° C.]: −5.4. Cp: fitted data 2.2° C.

Following the synthesis process in Example 4, the compounds below were synthesized with different raw materials, which had the following performance parameters:

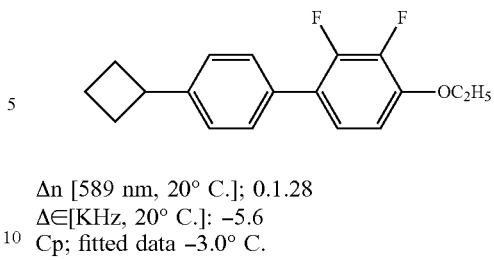

Δn [589 nm, 20° C.]; 0.1.28
Δ∈[KHz, 20° C.]: −5.6
Cp; fitted data −3.0° C.

Example 5

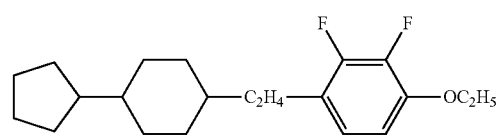

Step 1:

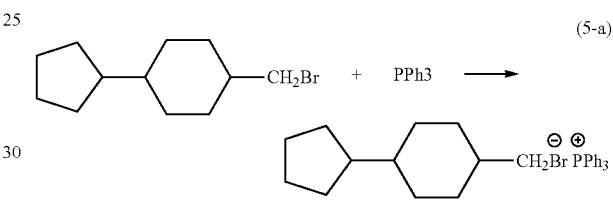

49 g (0.2 mol) (2-a) (n=0) and 57.6 g triphenylphosphine were dissolved together in 200 ml toluene, heated to reflux for 6 hrs, and then cooled to room temperature. The precipitated solid was filtered off, to obtain 71 g of a white solid. Yield; 70%.

Step 2:

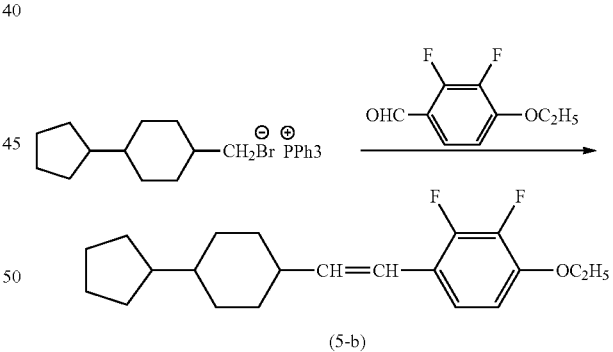

50.7 g (0.1 mol) of the phosphonium salt and 200 ml tetrahydrofuran were cooled to −10° C. together, and then 11.2 g (0.1 mol) potassium tert-butoxide was added while the temperature was controlled below 0° C., to obtain a yellow solution. A solution of 16.7 g (0.09 mol) 4-ethoxy-2,3-difluorobenzaldehyde in 30 ml tetrahydrofuran was added dropwise, and then reacted for 4 hrs after addition. The reaction solution was poured into 400 ml water, and the organic phase was separated. The aqueous phase was extracted with 100 ml ethyl acetate. The organic phases were combined, washed with water (1×), evaporated under reduced pressure to completely remove the solvent, extracted with petroleum ether (100 ml×4), purified by silica gel column chromatography, and recrystallized in ethanol, to obtain 18 g of a white crystal (5-b), Yield: 60%.

Step 3:

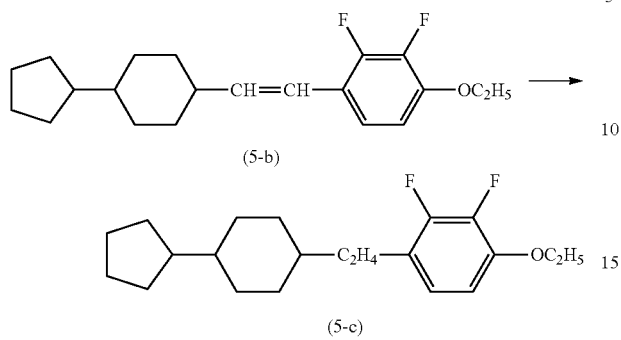

(5-b)

(5-c)

18 g (5-b) was dissolved in 100 ml toluene and 50 ml ethanol added with 0.5 g. Pd/C, and hydrogenated for 6 hrs under normal pressure until the theoretical hydrogen absorption is attained. Then the Pd/C was filtered off, and the filtrate was purified by silica gel column chromatography, and then recrystallized in petroleum ether, to obtain 1.5 g of a white crystal (5-c). Yield: 83%, Δn [589 nm, 20° C.]: 0.112. Δ∈[KHz, 20° C.]: −5.1. Cp: fitted data 21° C.

Following the synthesis process in Example 5, the compounds below were synthesized with different raw materials, which had the following performance parameters:

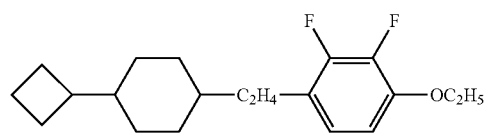

Δn [589 nm, 20° C.]: 0.108
Δ∈[KHz, 20° C.]: −5.0
Cp: fitted data 18° C.

Example 6

Liquid Crystal Mixtures a and b

Components A and B were uniformly mixed, to obtain a liquid crystal mixture a. Component A comprises 17 parts by weight of

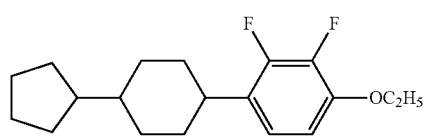

prepared in Example 1, and 10 parts by weight of

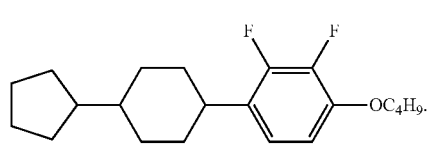

Component B comprises, in parts by weight:

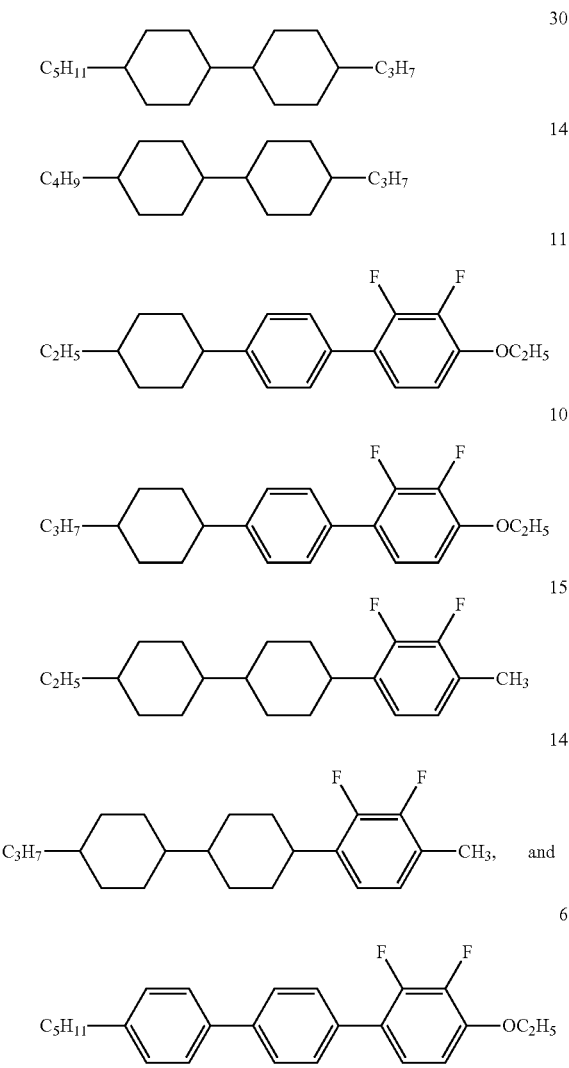

Component B has the following liquid crystal properties;
Δn [589 nm, 20° C.]: 0.097
Δ∈[KHz, 20° C.]: −3.1
Cp: 118.8° C.

Liquid crystal mixture a has the following liquid crystal performances:
Δn [589 nm, 20° C.]: 0.096
Δ∈[KHz, 20° C.]: −3.6
Cp: 81.6° C.

In component A of the liquid crystal mixture a above was replaced by equivalent parts of

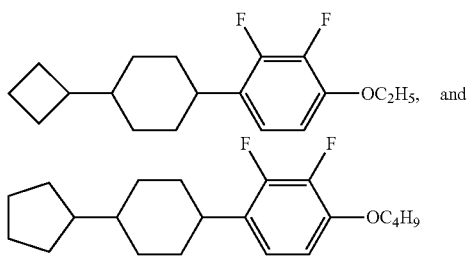 and

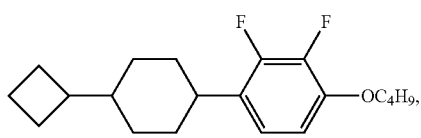

was replaced by equivalent parts of

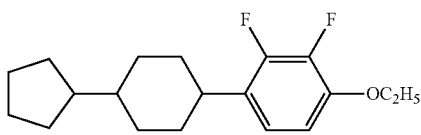 [SMILES: CCOc1ccc(C2CCC(C3CCCC3)CC2)c(F)c1F]

to obtain a liquid crystal mixture b.

Liquid crystal mixture b had the following liquid crystal properties:
Δn [589 nm, 20° C.]: 0.095
Δ∈[KHz, 20° C.]: −3.7
Cp: 81.4° C.

Comparative Example 1

Liquid Crystal Mixtures a' and b'

The compound

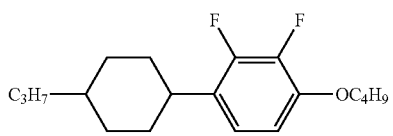

of Formula I in Example 6 was replaced by equivalent parts of the compound

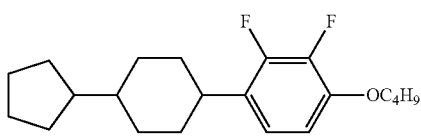

having alkyl as a terminal group (Cp: fitted data −10° C.), and the compound

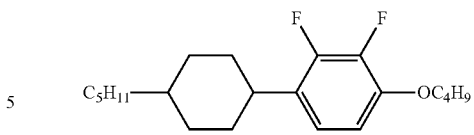

of Formula I was replaced by equivalent parts of the compound

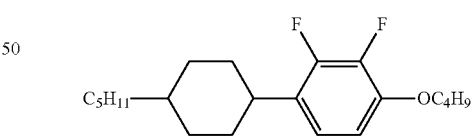

having alkyl as a terminal group (Cp: fitted data −11° C.), to obtain a liquid crystal mixture a', which had the following liquid crystal properties;
Δn [589 nm, 20° C.]: 0.09
Δ∈[KHz, 20° C.]: −3.4
Cp: 77.0° C.

The compound

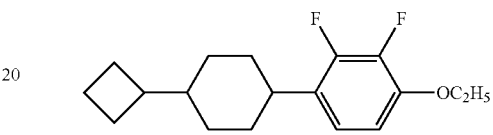

of Formula I in Example 6 was replaced by equivalent parts of the compound

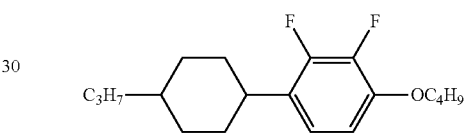

having alkyl as a terminal group (Cp: fitted data −10° C.), and the compound

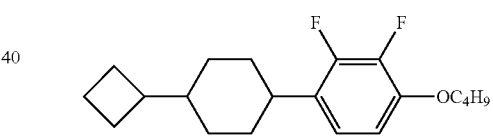

of Formula I was replaced by equivalent parts of the compound

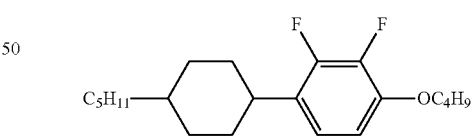

having alkyl as a terminal group (Cp: fitted data −11° C.), to obtain a liquid crystal mixture b'. The liquid crystal properties thereof are not significantly different from those of the liquid crystal mixture a', and are not elaborated herein again.

It is shows from Example 6 and Comparative Example 1 that, the clearing point Cp and the absolute value of the negative dielectric constant Δ∈ of the liquid crystal mixtures a and b with the compound of Formula I prepared in Example 1 of the present invention are obviously higher than those of the liquid crystal mixtures a' and b' with equivalent parts of the liquid crystal compounds having alkyl as the terminal group.

Example 7

Liquid Crystal Mixture c

A liquid crystal mixture c was obtained with the formulation ratio of the liquid crystal mixture in Example 6, except that

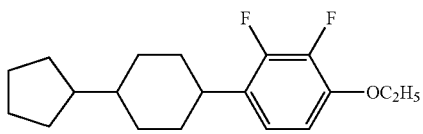

was replaced by

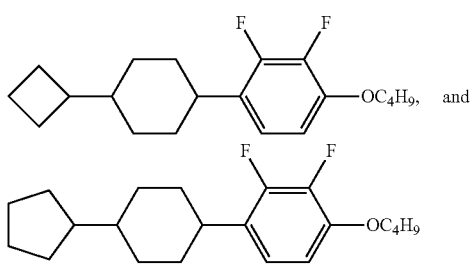
and was replaced by

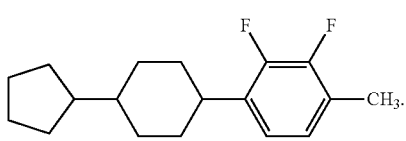 [SMILES: Cc1ccc(C2CCC(C3CCCC3)CC2)c(F)c1F]

A liquid crystal mixture c' was obtained with the formulation ratio of the liquid crystal mixture in Comparative Example 1, except that

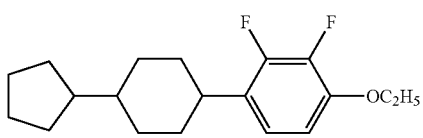

was replaced by

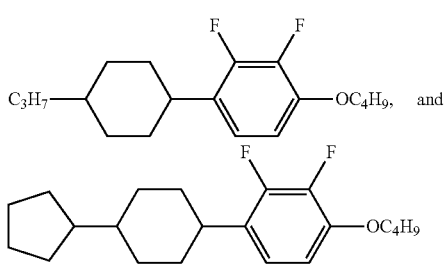
and was replaced by

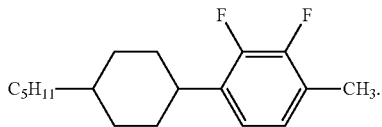

The detection results of the liquid crystal properties of the liquid crystal mixtures c and c' are not significantly different from those of the liquid crystal mixtures a and a', and are not elaborated herein again.

Example 8

Liquid Crystal Mixture d

A liquid crystal mixture d1 or d2 was obtained with the formulation ratio of the liquid crystal mixture in Example 6, except that 17 parts by weight of

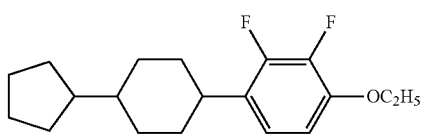

was replaced by 27 parts by weight of

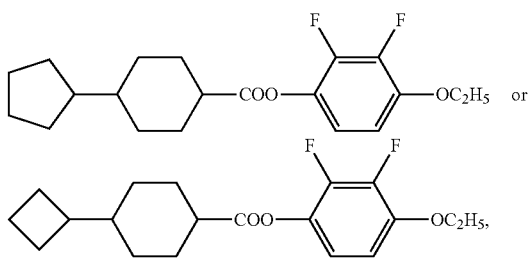

and 10 parts by weight of

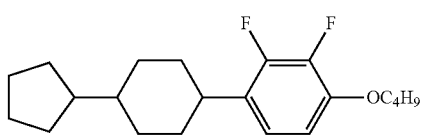

was omitted.

A liquid crystal compound d' was obtained with the formulation ratio of the liquid crystal mixture in Comparative Example 1, except that

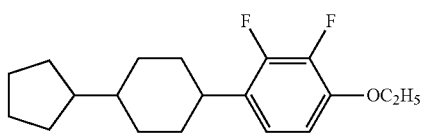

was replaced by 27 parts by weight of

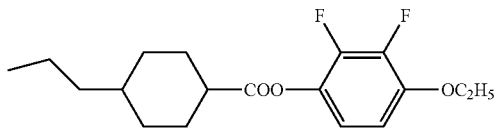

(Cp: fitted data 52.6° C.), and the component

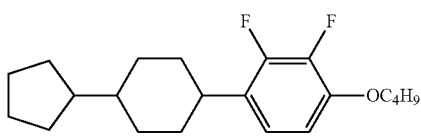

was omitted.

The detection results of the liquid crystal performances of the liquid crystal mixtures d1 or d2 and d' are not significantly different from those of the liquid crystal mixtures a and a', and are not elaborated herein again.

Example 9

Liquid Crystal Mixture e

A liquid crystal mixture e1 or e2 was obtained with the formulation ratio of the liquid crystal mixture in Example 6, except that 17 parts by weight of

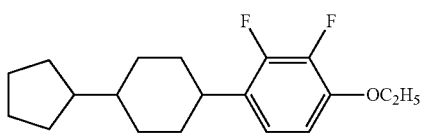

was replaced by 27 parts by weight of

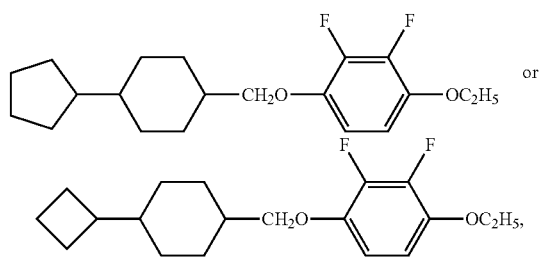

and 10 parts by weight of

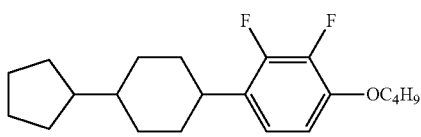

was omitted.

A liquid crystal compound e' was obtained with the formulation ratio of the liquid crystal mixture in Comparative Example 1, except that

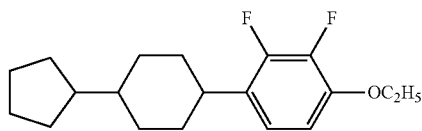

was replaced by 27 parts by weight of

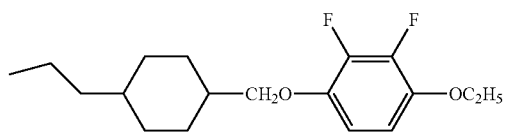

(Cp: fitted data −6.0° C.), and the

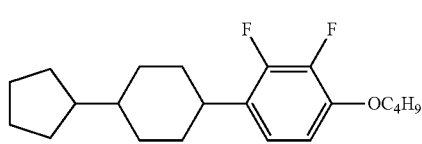

was omitted.

The detection results of the liquid crystal properties of the liquid crystal mixtures e1, e2 and e' are not significantly different from those of the liquid crystal mixtures a and a' and are not elaborated herein again.

Example 10

Liquid Crystal Mixture f

A liquid crystal mixture f1 or f2 was obtained with the formulation ratio of the liquid crystal mixture in Example 6, except that 17 parts by weight of

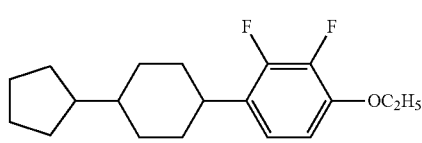

was replaced by 27 parts by weight of

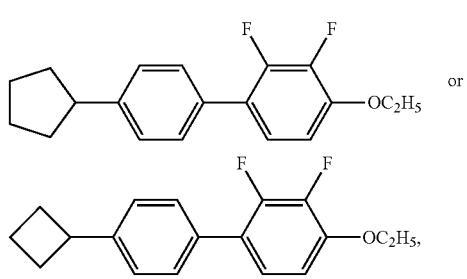

and 10 parts by weight of

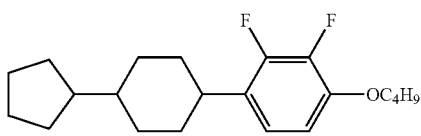

was omitted.

A liquid crystal compound f' was obtained with the formulation ratio of the liquid crystal mixture in Comparative Example 1, except that

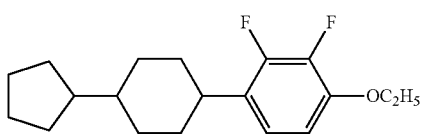

was replaced by 27 parts by weight of

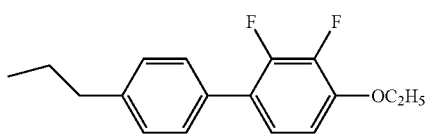 [SMILES: CCCc1ccc(-c2ccc(OCC)c(F)c2F)cc1]

(Cp: fitted data −14° C.), and the component

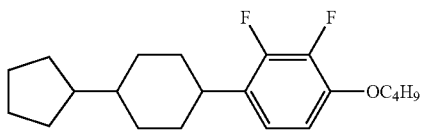

was omitted.

The detection results of the liquid crystal properties of the liquid crystal mixtures f1, f2 and f' are not significantly different from those of the liquid crystal mixtures a and a', and are not elaborated herein again.

Example 11

Liquid Crystal Mixture g

A liquid crystal mixture g1 or g2 was obtained with the formulation ratio of the liquid crystal mixture in Example 6, except that 17 parts by weight of

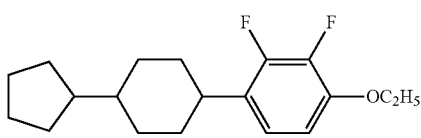

was replaced by 27 parts by weight of

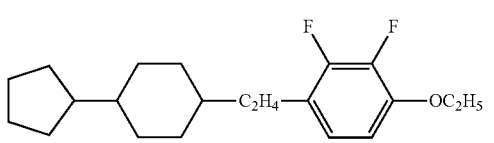

or

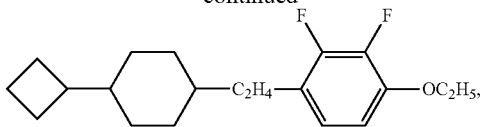

and 10 parts by weight of

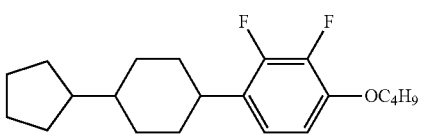

was omitted.

A liquid crystal compound g' was obtained with the formulation ratio of the liquid crystal mixture in Comparative Example 1, except that

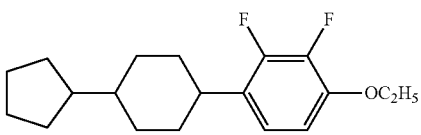

was replaced by 27 parts by weight of

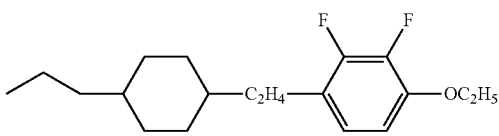

(Cp: fitted data −4° C.), and the component

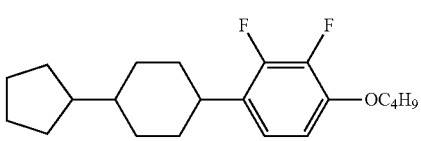

was omitted.

The detection results of the liquid crystal properties of the liquid crystal mixtures g1, g2 and g' are not significantly different from those of the liquid crystal mixture a and a', and are not elaborated herein again.

INDUSTRIAL APPLICABILITY

The negative dielectric anisotropic liquid crystal compound containing 2,3-difluorophenyl provided in the present invention has a negative dielectric anisotropy (Δ∈), and has cyclobutyl or cyclopentyl as a terminal group. Compared with conventional liquid crystal compounds with a flexible alkyl chain as a terminal group, the compound of Formula I according to the present invention has the advantage of high clearing point, and enables extension of the application range of a liquid crystal mixture because a positive correlation exists between the clearing points of the liquid crystal mixture and monomer liquid crystal compounds. In addition, such a compound can increase the absolute value of the

What is claimed is:
1. A compound of Formula I:

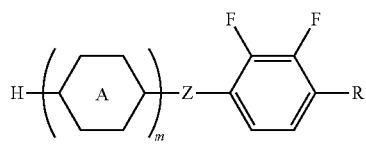

Formula I wherein H is cyclopentyl;

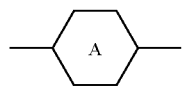

is selected from 1,4-phenylene, 1,4-phenylene substituted with fluoro, 1,4-cyclohexyl, and 1,4-cyclohexyl in which one or two —$CH_2$— is substituted with O;
Z is selected from a single bond, —COO—, —$CH_2O$—, and —$CH_2CH_2$—;
R is selected from C1-C6 alkyl and C1-C6 alkoxy; and
m is 1 or 2.

2. The compound according to claim 1, wherein the compound is one of Formulas I1 to I9 below:

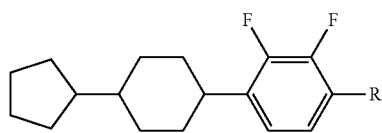 (I1)

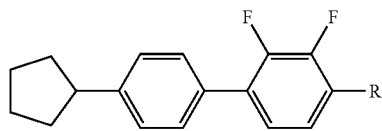 (I2)

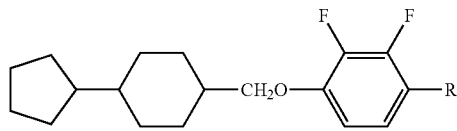 (I3)

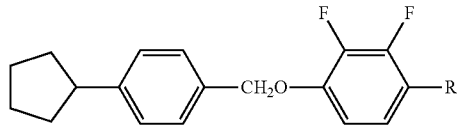 (I4)

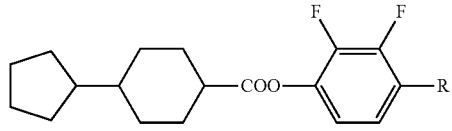 (I5)

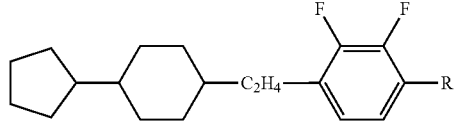 (I6)

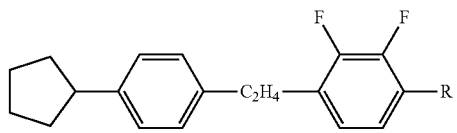 (I7)

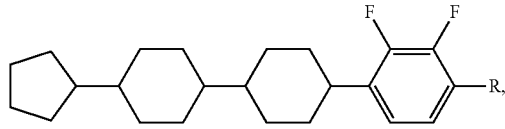 (I8), and

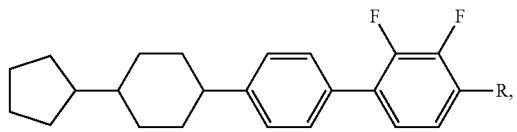 (I9)

wherein R is C1-C6 alkoxy.

3. A method of adjusting at least one of clearing point and negative dielectric constant of a liquid crystal mixture, comprising a step of adding a compound of Formula I according to claim 1.

4. The method of claim 3, wherein adjusting the clearing point of the liquid crystal mixture is increasing the clearing point of the liquid crystal mixture.

5. The method of claim 3, wherein adjusting the negative dielectric constant of the liquid crystal mixture is increasing the negative dielectric constant of the liquid crystal mixture.

6. A method of preparing a liquid crystal display material or electrooptical display material, comprising a step of adding a compound of Formula I according to claim 1.

7. A liquid crystal mixture comprising at least one compound of Formula I and a second component, Formula I wherein the second component comprises 1) at least one compound of Formula II and at least one compound of Formula III; or 2) at least one compound of Formula II, at least one compound of Formula III, and at least one compound of Formula IV, Formula II Formula III Formula IV

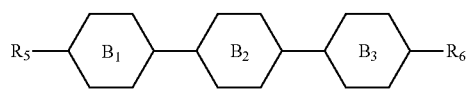

wherein H is cyclopentyl;

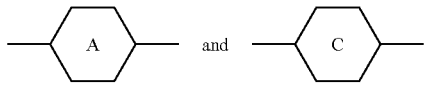

are each independently 1,4-phenylene, 1,4-phenylene substituted with fluoro, 1,4-cyclohexyl, or 1,4-cyclohexyl in which one or two —$CH_2$— is substituted with O;

Z is a single bond, —COO—, —$CH_2$O—, or —$CH_2CH_2$—;

R, $R_1$, $R_3$, $R_4$ and $R_5$ are each independently a C1-C6 alkyl or a C1-C6 alkoxy;

m and n are each independently 1 or 2;

$R_2$ and $R_6$ are each independently a C1-C6 alkyl or C2-C6 alkenyl;

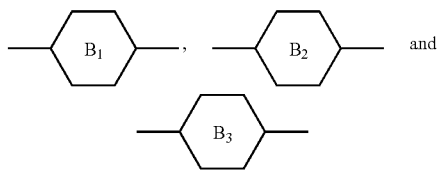

are each independently 1,4-phenylene or 1,4-phenylene substituted with fluoro; and a weight ratio of the compounds of Formula II and Formula III is 5-50:50-95, or a weight ratio the compounds of Formula II, Formula III and Formula IV is 5-50:50-95:1-5.

8. The liquid crystal mixture of claim 7, wherein the at least one compound of Formula I is selected from the compounds below:

(I1)
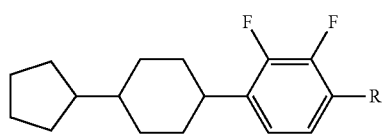

(I2)
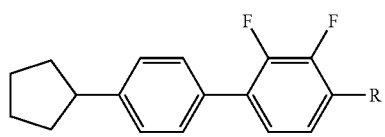

(I3)
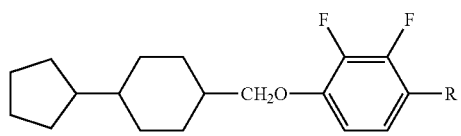

(I4)
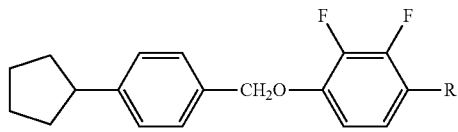

(I5)
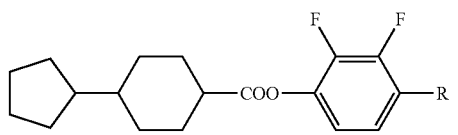

(I6)
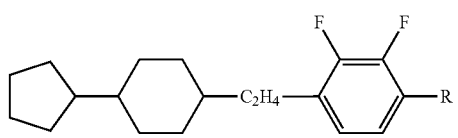

(I7)
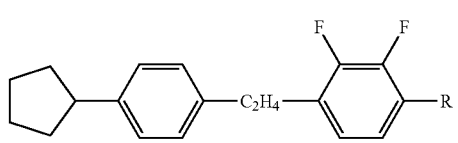

(I8)
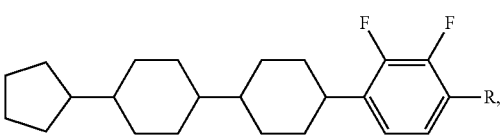

and (I9)
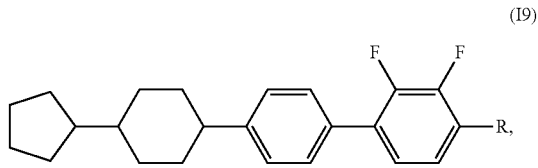

wherein R is C1-C6 alkoxy.

9. The liquid crystal mixture of claim 7, wherein each of the at least one compound of Formula I is 1-30% by weight based on a total weight of the liquid crystal mixture.

10. The liquid crystal mixture of claim 7, wherein the at least one compound of Formula I is 1-60% by weight based on a total weight of the liquid crystal mixture.

11. The liquid crystal mixture of claim 7, wherein the second component comprises the following compounds in a weight ratio given below:

30
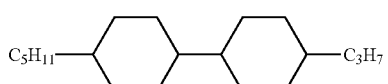

14
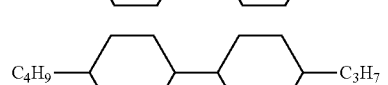

11
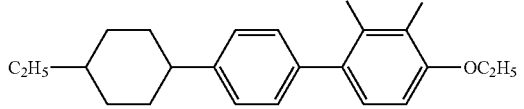

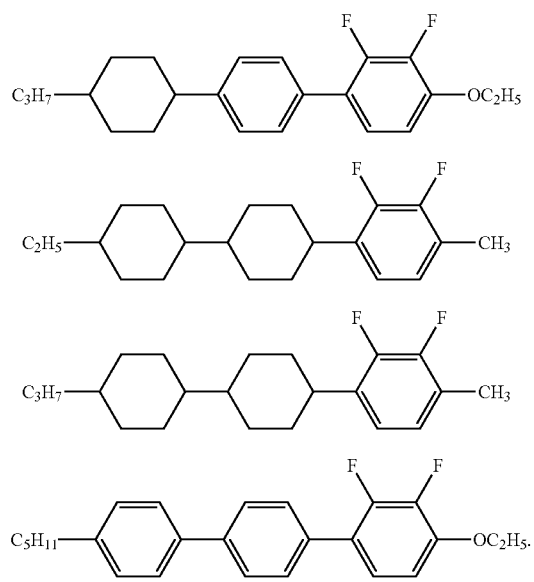

12. The liquid crystal mixture of claim 11, wherein the at least one compound of Formula I is one of the following in a weight ratio given relative to a weight of 100 for the second component of claim 11:

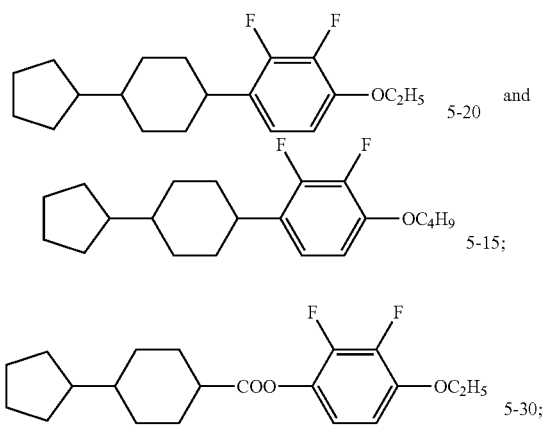

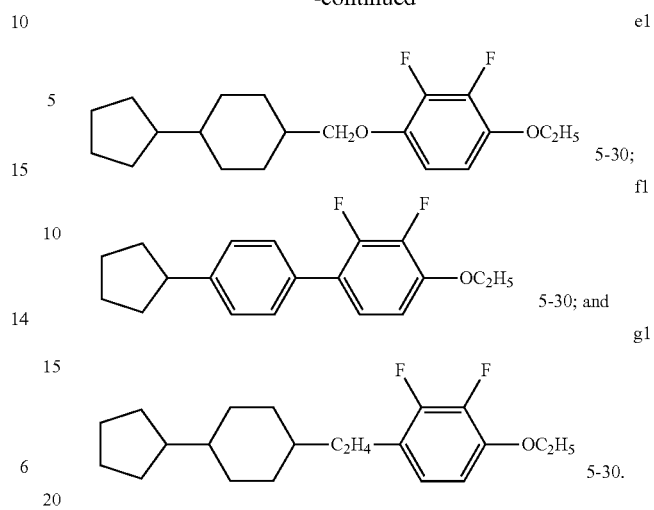

13. The liquid crystal mixture of claim 12, wherein the at least one compound of Formula I is one of the following in a weight ratio given relative to a weight of 100 for the second component of claim 11:

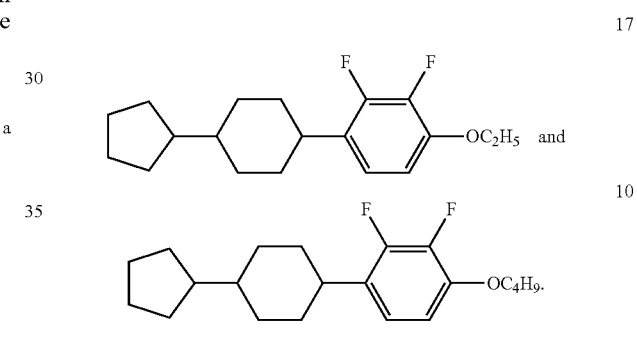

14. The liquid crystal mixture of claim 13, wherein a weight of d1, e1, f1, or g1 is 27 relative to a weight of 100 for the second component of claim 11.

15. A method of preparing a liquid crystal display material or electrooptical display material, comprising a step of adding the liquid crystal mixture of claim 7.

\* \* \* \* \*